United States Patent [19]
Sakurada et al.

[11] Patent Number: 6,004,667
[45] Date of Patent: *Dec. 21, 1999

[54] LOW TEMPERATURE MELT INJECTED ANTI-MICROBIAL FILMS, ARTICLES CONTAINING SUCH FILMS AND METHODS OF MANUFACTURE AND USE THEREOF

[75] Inventors: Tsukasa Sakurada, Nagano-ken; Akihiko Hashimoto, Higashi-ku, both of Japan

[73] Assignee: ShinShu Ceramics Company, Ltd., Nagano-Ken, Japan

[ * ] Notice: This patent is subject to a terminal disclaimer.

[21] Appl. No.: 08/269,174

[22] Filed: Jun. 30, 1994

[51] Int. Cl.$^6$ ........................................... B32B 5/16
[52] U.S. Cl. ..................... 428/323; 428/328; 428/403; 435/32
[58] Field of Search ................................. 428/323, 403, 428/328; 435/32

[56] References Cited

U.S. PATENT DOCUMENTS

| | | | |
|---|---|---|---|
| 4,817,594 | 4/1989 | Juhasz | 128/155 |
| 4,847,231 | 7/1989 | GrÄtzel et al. | 502/74 |
| 4,886,505 | 12/1989 | Haynes et al. | 604/265 |
| 4,892,712 | 1/1990 | Robertson et al. | 422/186 |
| 5,006,248 | 4/1991 | Anderson et al. | 210/500.25 |
| 5,028,568 | 7/1991 | Anderson et al. | 501/12 |
| 5,035,784 | 7/1991 | Anderson et al. | 204/158.14 |
| 5,104,539 | 4/1992 | Anderson et al. | 210/500.25 |
| 5,118,422 | 6/1992 | Cooper et al. | 210/636 |
| 5,126,111 | 6/1992 | Al-Ekabi et al. | 422/186.3 |
| 5,130,031 | 7/1992 | Johnston | 210/748 |
| 5,192,452 | 3/1993 | Mitsui et al. | 210/760 |
| 5,194,161 | 3/1993 | Heller et al. | 210/748 |
| 5,227,342 | 7/1993 | Anderson et al. | 501/12 |
| 5,238,749 | 8/1993 | Cueman et al. | 428/441 |
| 5,260,036 | 11/1993 | Weigold et al. | 422/186.3 |
| 5,269,926 | 12/1993 | Webster et al. | 210/500.25 |
| 5,308,454 | 5/1994 | Anderson | 204/59 R |
| 5,454,886 | 10/1995 | Burrell et al. | 148/565 |
| 5,470,585 | 11/1995 | Gilchrist | 424/604 |
| 5,541,233 | 7/1996 | Roenigk | 521/54 |

FOREIGN PATENT DOCUMENTS

| | | |
|---|---|---|
| S61-190059 | 8/1986 | Japan . |
| S61-190063 | 8/1986 | Japan . |
| H1-71414 | 1/1991 | Japan . |

OTHER PUBLICATIONS

Kogyo Zairyo, The Backgrounds in the Development of the Low–temperature Melt Injection Method, and its applications, 40(12), Oct., 1992, pp. 99–108.

Kogyo Zairyo, "Low–temperature Melt Injection Technique as a Means of Kin–Group Suppression", 41(9), Jul., 1993, pp. 107–115.

*Primary Examiner*—H. Thi Le
*Attorney, Agent, or Firm*—Wolf, Greenfield & Sacks, P. C.

[57] ABSTRACT

An article having anti-microbial properties which includes a low temperature melt injected film containing an interconnected network of resolidified photosemiconductor and conductor particles. The anti-microbial film also may include adsorbent particles for adsorbing microorganisms. Methods of manufacture of such articles, methods for treating infections, and methods for sterilizing fluids, also are provided.

34 Claims, 20 Drawing Sheets

LOW TEMPERATURE MELT INJECTED ANTI-MICROBIAL FILMS, ARTICLES CONTAINING SUCH FILMS AND METHODS OF MANUFACTURE AND USE THEREOF

FILED OF THE INVENTION

The present invention relates to low temperature melt injected anti-microbial films, specifically films including photosemiconductor and conductor particles, articles containing such films and methods of manufacture and use thereof.

BACKGROUND OF THE INVENTION

The sterilization of various bacteria, viruses and other microorganisms and the growth suppression of plants and algae is essential for many medical treatments, preventive hygiene, food processing and preservation, and industrial and domestic applications. Known sterilization techniques employ heat, electricity, microwaves, radiation, chemicals, toxicants, antibiotics, cold, ultraviolet and far-infrared rays, and high magnetic fields. Such sterilization techniques, however, generally require large equipment and/or facilities, and may damage the object being sterilized or become toxic to the patient undergoing treatment.

It has been proposed to employ photocatalytic materials (also referred to as photosemiconductors), such as titania ($TiO_2$), as membranes and filters to eliminate organic pollutants and other impurities from a fluid source such as water. UV irradiation of the photocatalytic material in water at an appropriate wavelength (less than 400 nm for titania) generates excess electrons in the conduction band leaving behind positively charged holes in the valence band. It is suggested in U.S. Pat. Nos. 5,126,111 and 5,118,422 that the oxidizing holes generated in the valence band react with adsorbed $H_2O$ or surface $OH^-$ groups to form extremely reactive OH radicals. The electrons react with molecular oxygen to form superoxide ions ($O_2$—) which subsequently leads to the formation of additional OH radicals. The OH radicals are considered essential to purification of the contaminated fluid.

The apparent choice of the prior art has been to form such photoreactive ceramic membranes in a sol-gel process which involves precipitation of a sol containing titania in solution (typically water or alcohol), removal of the solvent to create a semisolid gel and then calcination of the gel until a rigid porous membrane is formed. The ceramic membrane may be self-supporting or coated onto a mesh substrate prior to gellation. U.S. Pat. Nos. 5,227,342, 5,192,452, 5,035,784 and 4,892,712 are representative of conventional sol-gel formed photosemiconductor membranes. The sol-gel process suffers from several deficiencies. It is complicated, time consuming and expensive. The sol-gel process is not believed to be indicated for use with substrates made of paper, low melting point plastic mesh or other heat susceptible or liquid absorbable material which may be weakened, damaged or destroyed by the soaking, evaporating and firing steps required in sol-gel formation. The fired sol-gel membranes are likely to be brittle and susceptible to flaking and other deterioration of the photosemiconductive material, particularly after prolonged contact with the fluid being purified. Further, it would appear to be difficult to provide a porous membrane, necessary for filtration, having the required mechanical strength. Although sintering will stabilize the ceramic, the downside is a reduction in porosity due to grain growth.

An alternative and more advantageous approach for forming photocatalytic materials is generally described by Sakurada in Japanese patent nos. H3-60911, H3-65430 and H3-8448. Low temperature melt injection (LMI) is employed to create a thin, porous and flexible film of a particulate photosemiconductor on a heat susceptible substrate such as cloth, paper or plastic, previously electroless plated with a conductive metal such as nickel, without thermally damaging the substrate. The excited conduction band electrons, upon irradiation of the photosemiconductor film, migrate to the conductive metal where they act as a reducing agent. The positively charged holes in the photosemiconductor operate as an oxidizing agent. Organic materials, such as bacteria and viruses, which come into contact with the cloth are eliminated. When the film is immersed in water, the active species generated on the surface of the photosemiconductor particles and the electroless silver plated cloth migrate in the water to attack spatially separated microorganisms which are not within the intimate reach of the reactive surfaces. The photosemiconductor film and electroless plated substrate provide an improved sterilizing efficiency as compared to the photosemiconductor film alone. The metal conductor is believed to act as an electron attractor, delaying recombination of the conduction band electrons and valence band holes which are essential to destruction of the offending substances. Alternatively, the Sakurada references proposed coating the photosemiconductor particles with platinum or ruthenium oxide and then melt spraying the particles onto a mesh substrate.

The LMI technique involves entraining the fine photosemiconductor particles in a fast moving combustible carrier gas, igniting the gas to form a flame which melts the fine particles and carries the molten mist at high speed onto a cloth or other heat susceptible substrate. A cold accelerating gas injected from side ports jettisons the molten particles toward the substrate. The fine molten particles penetrate into and coat the mesh fibers of the substrate and then solidify very quickly, forming a binderless, flexible and porous photocatalytic film. Despite the fact that the ultrafine particles are melted at temperatures in excess of 1000° C., and sometimes as high as 3000° C., a heat susceptible substrate such as cloth or paper does not become damaged. LMI is simpler, faster and less expensive than the sol-gel process described in the aforementioned prior art, and results in a flexible, yet durable, photocatalytic film which can be coated onto thermally frail materials without adverse consequences. The high porosity of the LMI film enhances catalysis which is surface area dependent.

Investigation of the LMI process has revealed that the ability to adsorb microorganisms from a fluid to allow sufficient time for sterilization of the antimicrobial film would be beneficial. It also has been discovered by applicants that the reactive ability of the anti-microbial film can be enhanced by ensuring that an aqueous environment is maintained around the sterilizing material. The versatility and efficiency of the prior art LMI anti-microbial films also were believed to be enhanceable. It was not apparent from the prior art how to accomplish these newly discovered goals, which are achieved by the present invention as delineated below.

SUMMARY OF THE INVENTION

The present invention is a porous antimicrobial film containing interconnected particulates of one or more photosemiconductors and conductors which have been formed by LMI. The solidified LMI spray will adhere to virtually any surface (hereinafter generally referred to as a substrate) without adversely affecting the flexibility or ease of handling of the starting material. No binder is required to bond the component particles together, resulting in a film consisting entirely of ingredients active in the sterilization and growth suppression processes. The anti-microbial film is activated by a predetermined wavelength of light, producing powerful oxidizing and reducing agents which can destroy undesirable microorganisms including bacteria and viruses. The conductive metal particles may provide additional, and independent, sterilizing action which is not light-dependent, so that the film will continue to eradicate the undesirable forms even in darkness. Adsorbent particles may be included in the anti-microbial film to trap and hold the microorganisms until the electrochemical reactants can eliminate them. To take advantage of the improved sterilizing efficiency which occurs when water is present, water retaining materials may be united with the film as well as water and vapor impermeable traps to prevent fluid loss.

In one embodiment of the invention, a flexible cloth substrate which has been electroless plated with a conductor, such as silver, is coated with an LMI film containing photosemiconductor particulates, such as titania, and conductor particulates such as silver.

In another embodiment, the LMI film further includes adsorbents particle such as hydroxyapatite. The hydroxyapatite may be included in the same layer as the photosemiconductor and conductor particles or, preferably, will be contained in a separate layer which has been applied at a lower temperature to prevent decomposition of the OH groups which are essential to the trapping function. A conductive metal, such as silver, having a melting point lower than the dehydration temperature of concern, is flame sprayed with the hydroxyapatite to form a molten conductive glue which rapidly cools on contact with the substrate and binds the adsorbent particles in and near the photosemiconductor and conductor particulates. Additionally, it was observed that the adsorbent thermally fragments during LMI into large and small grains, with the small grains melting and forming a molten adhesive which support the melt resistant larger fragments upon cooling.

In another embodiment of the present invention, a hydrophillic material is provided as a base layer upon which the electroless plated cloth may be overlayed. A photosemiconductor and conductor particle film covers the cloth or is directly applied to the water retentive layer. An adsorbent and conductive metal layer may be included in the film. A water absorbing and permeable polymer sheet may be applied over the photosemiconductor and conductor layer to optimize the availability of water to the photocatalytic process. To prevent the fluid from leaking or evaporating, a water and vapor impermeable seal may be provided over the composite. An additional layer may be provided, or an extension of any of the already mentioned layers, which includes an adhesive for securing the composite to the skin when the device is used as a bandage or wound dressing.

It is an object of the invention to provide an article with anti-microbial properties that is safe, non-toxic and effective.

It is another object of the invention to provide an article that has anti-microbial properties both in the presence and absence of light.

It is another object of the invention to provide an article that has both microbial adsorbing and anti-microbial properties.

It is another object of the invention to provide a cloth with anti-microbial properties that is flexible and easy to handle.

It is another object of the invention to provide a bandage that is effective in treating and preventing infections of wounds.

It is another object of the invention to provide a bandage that is effective in killing microorganisms that are resistant to other types of anti-microbial agents.

It is another object of the invention to provide a bandage that remains moist for an extended period of time.

It is another object of the invention to provide a filter that is permeable to fluids and can be used for purification and sterilization of fluids with only a minimal number of applications.

The invention also includes a method for treating or preventing infection of a wound on a human or other organism in which an article described above is contacted with the wound for a period of time so as Lo effect treatment of the wound.

The invention also features a method for sterilizing a fluid in which an article described above is contacted with the fluid so as to effect sterilization by having the fluid pass through the article.

BRIEF DESCRIPTION OF THE DRAWINGS

The above and other objects, features and advantages of the present invention will be better understood from the following specification when read in conjunction with the accompanying drawings in which:

FIG. 3a is an SEM secondary electron image photomicrograph of a silver plated polyester fabric at 700×, while

DETAILED DESCRIPTION

Figure 1:
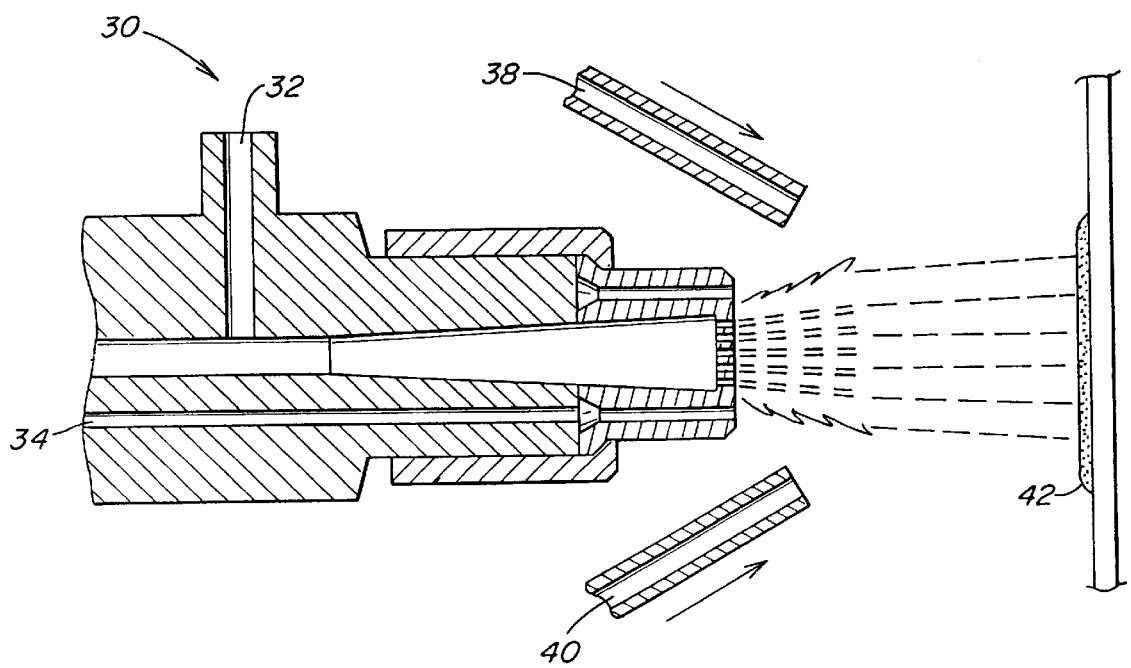
FIG. 1 is a schematic illustration of a gas melt injection torch for use in making an anti-microbial films in accordance with the present invention.

The present invention is a flexible and durable anti-microbial film which is applied by low temperature melt injection onto heat susceptible substrates, such as cloth, paper or plastic mesh, without thermally damaging or weakening the substrate. "Heat susceptible", for purposes of this application, means a material which thermally weakens (e.g. deforms, decomposes, melts, vaporizes, ignites, chemically reacts, oxidizes, undergoes structural or phase change) at temperatures above 100° C., rendering the material incapable of use as a substrate for the applications described herein. The film includes a mixture of ultrafine photosemiconductor and conductor particles which have been melted in a flame and sprayed as molten droplets onto the substrate. The molten mist rapidly solidifies, forming a thin porous film of intimately dispersed particles having a large specific surface area. The film is binderless, optimizing the particulate surface area available to achieve chemical breakdown of the undesirable microbes. As explained herein, the oxidizing and reducing activity occurs at the surface of the photosemiconductor and conductor particles so that an increase in surface area available to contact the microorganisms or an aqueous media in communication therewith will enhance the eradicating affect. The porous network of fused particles provide a pathway for fluid to travel completely through the film. Although durable, the film is compliant and will allow the substrate to retain its uncoated flexibility. Although the film may be coated on virtually any surface susceptible to harboring bacteria or viruses, it is especially centemplated that the anti-microbial film wall have application as a bandage or dressing for reducing the incidence of bacteria in wounds and as a filter for purifying water and air.

The photosemiconductor and conductor particulate film has proven especially useful at sterilizing bacteria and viruses and at suppressing the growth of fungi, algae and other microorganisms. For purposes of this application, the term "anti-microbial" is intended to broadly mean either the killing or growth suppression of such undesirable forms. The photosemiconductor and conductor particles form an electrochemical cell, actually thousands of tiny randomly dispersed electrochemical cells, which are activated by irradiation with a predetermined wavelength of light. Sources of light that can be used for activation include fluorescent lamps, sunlight, or any other light source which provides the necessary wavelength for the particular photosemiconductor selected. Oxidizing and reducing agents at or near the surface of the particles create extremely effective ions and molecules for eliminating undesirable forms within the sterilizing reach of the film or in a fluid media in contact with the film. Recombination of the conduction band electrons and valence band holes, which is known to limit anti-microbial action, is impeded by the conductor which functions as a charge separator. Accordingly, the anti-microbial action of the present composite photosemiconductor/conductor film is greatly enhanced as compared to a film consisting solely of the photosemiconductor.

A variety of photosemiconductor particles are contemplated for use in the inventive film including $TiO_2$, $KNbO_3$, $SrTiO_3$, CdSe, CdS, $WO_3$, and $Fe_2O_3$. Other photoreactive ceramics also are contemplated as would be apparent to those of skill in the art. A preferred photosemiconductor is $TiO_2$ which has been shown to be non-toxic (Sakamoto, M., Ceramics 21(4); 312, 1986), and therefore is particularly suitable for medical and other uses which require contact or ingestion by living organisms. Titanic exerts enhanced catalytic action because its energy level is deeper than other photocatalytic materials. Consequently, the oxidizing action of the positive holes generated by photoactivation is heightened. Where $TiO_2$ is employed as the photosemiconductor, it is preferable to use a fluorescent lamp as the light source, as wavelengths of about 400 nanometers are preferred for photoactivation of the $TiO_2$ which has a band gap of approximately 3.0 (eV).

Certain photosemiconductors when present in the photosemiconductor/conductor composite appear to have different spectrums of effectiveness in killing different types of microorganisms. For example, $KNbO_3$ is particularly effective in defeating methicillin resistant *Staphylococcus aureus*. The anti-microbial film may include a mixture of different types of photosemiconductor particles to allow use of the coating to eliminate a number of targets as opposed to simply a single undesirable microbe.

Silver and nickel are preferred conductive particles because they are resistant to oxidation which can occur during LMI and silver will form ions in solution which have known anti-microbial affect. Silver is particularly effective at killing bacteria and viruses whereas nickel is believed to be more effective against algae. Particularly significant is that exposure to light is not required for the metals to act as sterilizing agents. Consequently, a photosemiconductor/conductor particulate film containing silver will function to defeat bacteria, viruses or algae even in darkness, although at a slower rate than if the photochemical cell had been activated. It also is contemplated to employ a combination of conductive particles in the film, such as silver and nickel, to combat different spectrum of microorganisms. Other conductive particles, and mixtures thereof, also may be employed in the film as would be apparent to those of skill in the art.

Anti-microbial action by the photosemiconductor/conductor film generally does not occur instantaneously. This time constraint may be particularly acute when the film is used to filter a continuously flowing, non-recirculating, germ bearing fluid. The provision of bacteria or virus selective adsorbent particles in the film can improve the sterilization efficiency. The undesirable microorganisms are trapped by the adsorbents immediately as they pass through the film and are held in the film until they can be eliminated by the anti-microbial agents generated by the electrochemical cell. Adsorbents include apatite of the general composition $A_{10}(MO_4)_6X_2$, zeolite and activated carbon. A preferred adsorbent is hydroxyapatite, a calcium phosphate ceramic, which is known to be particularly adept at adsorbing viruses. An especially suitable hydroxyapatite is provided by Sekisui Chemical Processing Co., Ltd. which contains structural water $nH_2O$ in addition to the OH groups believed essential to adsorption. Example 1 demonstrates the absorption properties of hydroxyapatite. Other adsorbent particles are contemplated for use in the film as would be recognized by those of skill in the art.

The LMI anti-microbial coating may be applied to the surface of virtually any material and, where the material is porous, may be impregnated therein. As noted above, LMI will not thermally damage heat susceptible materials such as paper, cloth, thin metal film, glass or plastic. Preferably, the substrate is a flexible natural or synthetic cloth consisting of woven, knitted, braided or otherwise interengaged yarns, having interstices or pores between adjacent yarns, that become coated with the anti-microbial film. To facilitate acceptance of the LMI film, the substrate preferably is coated with an electroless plating of silver or other conductive metal. The thin metal coating appears to provide a base upon which the film can seed and grow as additional particles aggregate and solidify. While the film can be applied to substrates lacking the electroless plating, areas of the bare fiber have been observed microscopically where the film did not take hold. While it is expected that other coating techniques may be suitable, electroless plating is preferred as it uniformly covers the entire surface of the fibers, including those yarns located in difficult to access regions of the fabric. Silver is particularly attractive as the surface plating since it will provide anti-microbial action, even without exposure to light, in addition to serving as the primer for the anti-microbial film. Emicloth, an electroless silver plated unwoven acrylic cloth, available from Mitsubishi Metal Company has proven a satisfactory substrate. Other conductive materials also could be employed, including nickel which will provide the additional benefit of suppressing algae growth. Nickel containing metals such as stainless steel also are contemplated.

It has been discovered, as explained below in the Examples, that employing a water retaining substrate, or providing a water retaining material in addition to the substrate, enhances the photoreactive affect by allowing the active ions or molecules generated on the surfaces of the photoconductor and conductor particles to migrate through the water to attack bacteria and other undesirable microorganisms which are not in direct contact with the anti-microbial film. A preferred water retaining material is a silk based cloth, such as Kinuzu, which contains primarily silk fibroin and silk sericin. Silk fabric is attractive because it can be made of fine threads increasing the available surface area of the antimicrobial film, has moisture controlling characteristics, and absorbs undesirable molecules, e.g., ammonia, carbon dioxide, ethylene and putrefactive enzymes. The silk based cloth may be treated with chitosun, a derivative of chitin which is a polysaccharide contained in crab shells. Chitosun has anti-microbial properties, has no known side effects on skin, and decomposes slowly to harmless compounds.

While a fibrous or filamentous sheet has been described, it also is contemplated that other materials, solid or porous, and other configurations could be employed including coating a three dimensional substrate with the anti-microbial film or forming the preferred LMI coated cloth sheet into a three dimensional shape such as a cylinder or cone. Of course, the design and selection of such other materials and configurations would be application specific. Thus, the anti-microbial film also may be applied onto non-porous, inflexible, hard, heat-resistant surfaces. For example, it is contemplated that the substrate could include a bed of hydroxyapatite or alumina beads which are coated with the photosemiconductor/conductor particulate film and then provided in a filtering column for purifying and sterilizing liquids passed therethrough.

The LMI technique for applying the anti-microbial film is generally disclosed in applicant Sakurada's Japanese patent nos. H3-60911, H-65430 and H3-8448 and the article by Sakurada in Kogyo Zairyo 40(12): 99–108, 1992, which are incorporated herein by reference. To coat a cloth substrate with the LMI anti-microbial film, a mixture of the ultrafine photosemiconductor and conductor particles (preferably 90% photosemiconductor and 10% conductor by weight) are entrained in a carrier gas, such as acetylene, which may be mixed with oxygen and then combusted, forming tiny molten photosemiconductor and conductor droplets which are carried by the high velocity flame into the fibrous pattern of the cloth substrate. The extremely small particles, on the order of from about 5 to about 25 $\mu$m prior to melting, cool extremely fast so that the heat susceptible cloth substrate is not thermally damaged despite the fact that the flame temperature can be as high as 3000° C. depending upon the composition of the photosemiconductor and conductor particles.

FIG. 1 illustrates a gas melt injection torch 30 that can be used in LMI. The photosemiconductor and conductor particles enter torch 30 through a first inlet 32 which depends from a hopper or other source of the gas melt injectable material and become mixed with the carrier gas flowing through line 36. Oxygen running through line 34 is mixed with the carrier gas and then ignited. The fast moving and turbulent flame quickly melts and mixes the fine particles. Acceleration gas funneled from side ports 38 and 40 impels the molten mist into the fibrous substrate 42. The acceleration gas cools the droplets and the substrate although the photosemiconductor and conductor particles are believed still to be molten when they smash into the cloth fibers, spreading and diffusing between adjacent threads before they solidify. The resulting film consists of a porous network of partially connected, intimately mixed, photosemiconductor and conductor particles. The threads become encapsulated by the anti-microbial film although openings remain between the threads, ensuring that fluid can permeate through the film.

Figure 2A:
FIG. 2a is a reflect light photomicrograph of the surface of a $TiO_2$+Ag/Ag(acryl) cloth at 100×.
Figure 2B:
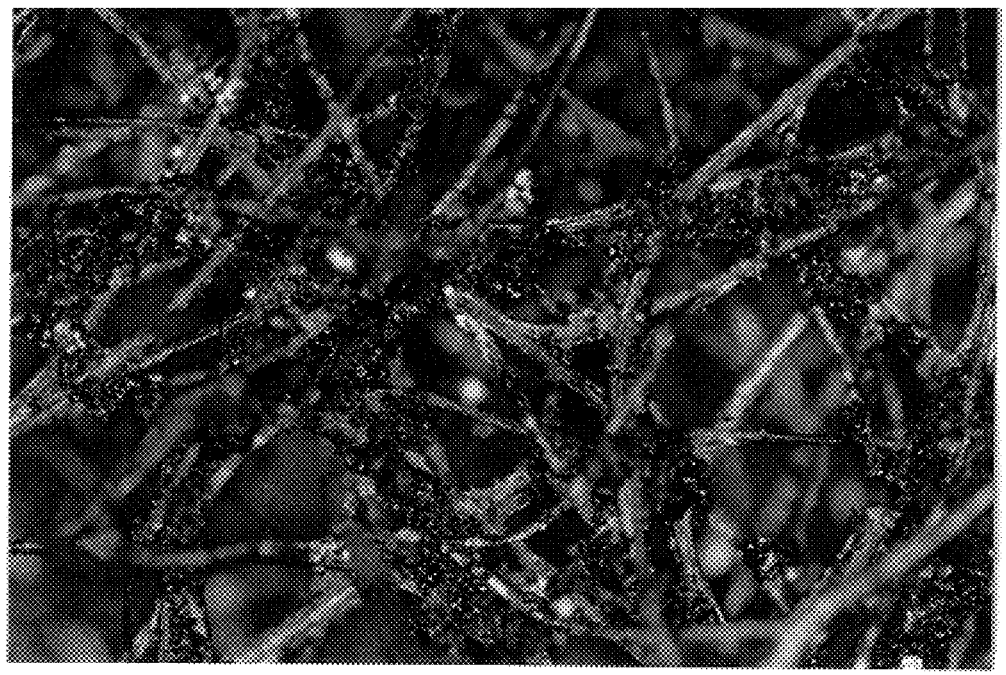
FIG. 2b is a reflective light photomicrography of the surface of a double layered $TiO_2$+Ag/HAp+Ag/Ag(acryl) cloth at 100×.

Examination under a reflection microscope reveals that the texture of the film is dependent upon the structure of the substrate onto which it is injected. Where the substrate is an essentially open and unwoven fabric, such as the acrylic cloth used in the Examples below, the molten particles are likely to solidify and aggregate at fiber junctions in the various random layers of the cloth, as shown in FIGS. 2a–2b. It is noted that acute triangular openings formed by randomly crossing filaments appear to provide an attractive base from which particle aggregation occurs. Less prevalent are grains which attach to essentially free or non-intersecting fibers. The particles, particularly in the outermost surface, seem irregular or lobate exhibiting elongated lumps particularly where a fiber is enclosed or encapsulated by the film.

Figure 3A:
Figure 3B:
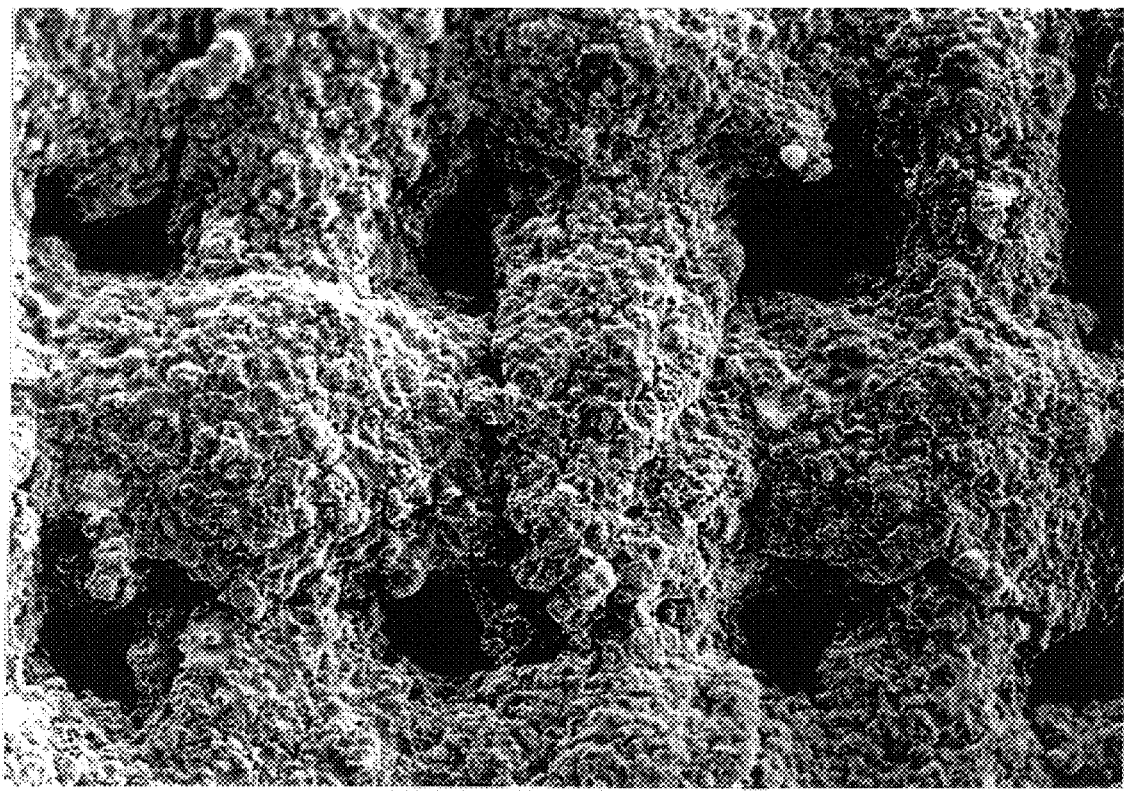
FIGS. 3b–c are SEMs of an anti-microbial film coated onto the polyester fabric at 700× and 4600×, respectively.
Figure 3C:
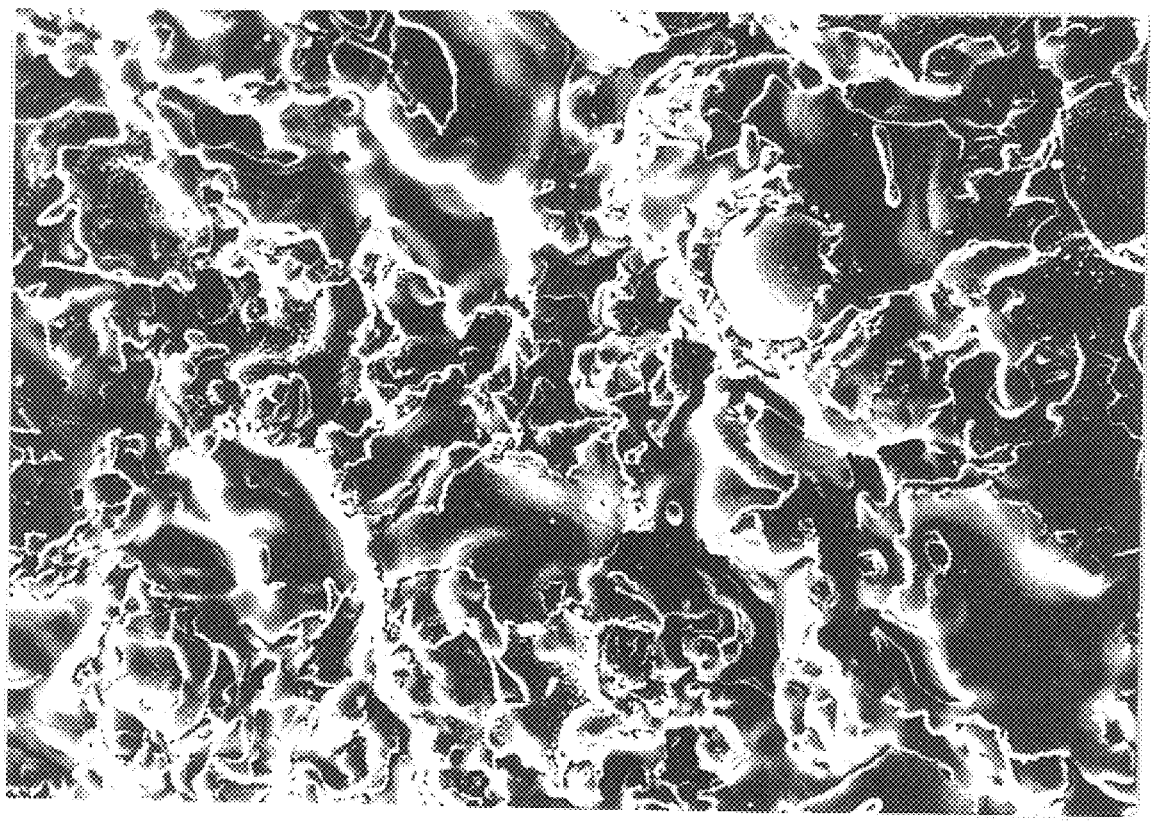

The surface of a coated, electroless Ag plated polyester fabric substrate is shown in FIGS. 3a–3c. In contrast to the acrylic substrate, the polyester cloth consists of organized bundles of tightly compacted threads (uncoated cloth illustrated in FIG. 3a). Presumably, the motion of the injected molten grains is halted by the tightly bundled threads, forming a film of flattened, cabbage shaped grains (i.e. multiple lobes) on the surface of the fabric. Molten lobes and fingers are believed to penetrate through narrow interstices between adjacent filaments where they then solidify and interlock. (See FIG. 3c). The texture of the film formed on the tightly woven polyester fabric is similar to the topography of films formed on flat, solid surfaces such as metal, plastic and paper. With solid metal and plastic substrates, it may be preferable to roughen the surface to enhance adherence of the LMI film.

Preferably, the photosemiconductor and conductor are mixed in particulate form and simultaneously melt injected onto the substrate. Alternatively, the conductor may be electroless plated onto the substrate and the photosemiconductor then melt injected thereover, as previously suggested in the above-noted Sakurada prior art. Where a plurality of photosemiconductor and/or conductor materials are employed (e.g., titania and strontium-titanium oxide as photosemiconductors and nickel and silver as conductors) the particles may by applied one component at a time, in a combination of particle types or with all the groups being melt injected simultaneously. In a further alternative embodiment, one or more of the different metal powders can be independently electroless plated onto the substrate, with the other metal(s) and photosemiconductor materials being subsequently melt injected onto the metal plated substrate.

The adsorbent also may be melt injected simultaneously with the photosemiconductor and conductor particles forming a single layer film. However, it is believed preferable to melt inject the adsorbent separately from the photosemiconductor because the melting temperature of the ceramic is higher than the decomposition temperature of the OH group believed to control the adsorption properties of the particle. Accordingly, it has been proposed, as demonstrated in the Examples below, to mix the adsorbent with a conductive metal which has a lower melting temperature than the decomposition temperature of the OH group, to form a molten conductive glue which, upon solidifying, will bind the adsorbent to the film without destroying the trapping action of the particle. The injection of hydroxyapatite as an adsorbent is illustrative. The OH base in hydroxyapatite which is believed essential to efficient adsorption will strip off at temperatures above 1000° C. $TiO_2$ particles must be heated to approximately 2000° C. before they will become molten. If the titania and hydroxyapatite are melt injected together, the high temperature required by the titania would render the hydroxyapatite anhydrous, destroying the species responsible for adsorption. To prevent dehydration of the hydroxyapatite, silver which has a melting point of 960° C., less than the critical decomposition temperature, is mixed with hydroxyapatite and flame sprayed at a temperature between 960° C. and 1000° C. The ductile silver grains create a porous glue which appears to hold the hydroxyapatite to the substrate or to a titania and silver film layer if previously applied to the substrate.

Figure 4A:
FIGS. 4a–b are reflective light photomicrographs of an HAp+Ag/Ag(acryl) cloth at 100× and 400×, respectively.
Figure 4B:

It appears that the hydroxyapatite itself may assist the silver in the bonding function, or actually be responsible therefore. As can be seen from the photomicrographs in FIGS. 4a–b, large unmelted hydroxyapatite grains (angular or euhedral) are present in the film along with smaller solidified previously molten grains. The small resolidified grains alone, or in conjunction with the remelted silver, secure the larger active hydroxyapatite fragments to the film. It is postulated that the hydroxyapatite particles fragment into large and small grains during LMI with only the small grains melting due to their lower heat capacity. The large and small fragments probably resulted from thermal stress of the large adsorbent particles (which had been formed by loose aggregation of submicron particles) during LMI.

Various arrangements of the photosemiconductor/conductor and adsorbent/conductor layers are contemplated. The photosemiconductor/conductor can be applied onto the electroless silver plated cloth upon which the adsorbent/conductor film is overlayed or, instead, the adsorbent/conductor coat can be applied first followed by the photosemiconductor/conductor layer. The latter arrangement has proven to be especially effective in killing methicillin-resistant Staphylococcus aureus, as shown in Example 5. It is believed that the hydroxyapatite layer adsorbs the bacteria, which in turn are killed by the adjacent photosemiconductor/conductor layer (titania and silver), which in turn replenishes the adsorption capacity of the hydroxyapatite layer. Alternatively, it is supposed that the adsorbent/conductor film and the photosemiconductor and conductor film could be applied on different regions of the substrate, so long as the films remained in conductive contact. For example, the two films could be sprayed on opposite faces of the substrate or on adjacent contiguous regions.

Representative LMI processing parameters appear below.

| Ranges for Low-Temperature Melt Injection | | |
|---|---|---|
| Temperature between 1000–2500° C. | Pressure (kg/cm$^2$) | Flow rate (m$^3$/hr) |
| acetylene | 0.5–2 | 0.5–3 |
| oxygen | 1–4 | 1–4 |
| acceleration air | 3–15 | 10–80 |

Injection material supply = 0–50 g/min
Grain size (before injection) = 3–60 μm
Distance from the injection nozzle to the substrate = 3–20 cm
Distance from the acceleration gas nozzle to the substrate = 2–19 cm

| Conditions for Formation of the TiO2 + Ag Film | | |
|---|---|---|
| T ~ 2000° C. | Pressure (kg/cm$^2$) | Flow rate (m$^3$/hr) |
| acetylene | ~1 | ~1.5 |
| oxygen | ~2 | ~2 |
| acceleration air | ~7 | ~40 |

Injection material supply = ~20 g/min
Grain size (before injection) = 5–25 pm (Ave. ~10 pm)
Distance from the injection nozzle ~7 cm
Distance from the acceleration nozzle ~6 cm

| Conditions for Formation of the HAp + Ag Film | | |
|---|---|---|
| T ~ 1000° C. | Pressure (kg/cm$^2$) | Flow rate (m$^3$/hr) |
| acetylene | ~1 | ~1.2 |
| oxygen | ~2 | ~1.6 |
| acceleration air | ~7 | ~40 |

Injection material supply = ~20 g/min
Grain size (before injection) = 25–40 pm (Ave. ~35 pm)
Distance from the injection nozzle ~7 cm
Distance from the acceleration nozzle ~6 cm The anti-microbial film can be applied as a coating on the surface of virtually any device or apparatus, solid or porous, for which freedom from bacteria, viruses and other undesirable microorganisms is desired. Without limitation, the following applications of the LMI anti-microbial film are contemplated: medical applications, e.g., bandages, dressings, plasters, and ointments for infection prevention and treatment, medical tools and devices, curtains, bedsheets, hospital gowns, floors, walls, doors, door knobs, telephones and air conditioners for preventive hygiene; environmental applications, e.g., air filters and water filters for purification or sterilization, e.g., of tanks, pools, cisterns, ponds, lakes, and drinking water; and food industry applications, e.g., food plant machine parts, food wrappers, inner linings of food containers and packages for manufacturing, processing, preservation and storage of fresh and canned foods.

Two preferred applications of the anti-microbial film, a filter or membrane and a bandage or wound dressing, are discussed below. By filter is meant any material which can function to separate or eliminate microbials from a fluid (liquid or gas). A natural or synthetic mesh fabric or screen is electroless plated with a thin silver layer. An LMI film containing partially connected, randomly mixed particulates of at least one photosemiconductor, such as titania, and at least one conductor, such as silver or nickel, is deposited onto the silver plated fibers. The film may include an adsorbent, e.g., hydroxyapatite, which preferably is provided as a separate layer sprayed at a lower melting temperature as described above. Multiple sheets of the LMI coated mesh may be overlayed or otherwise configured as required for filtration.

Figure 5A:
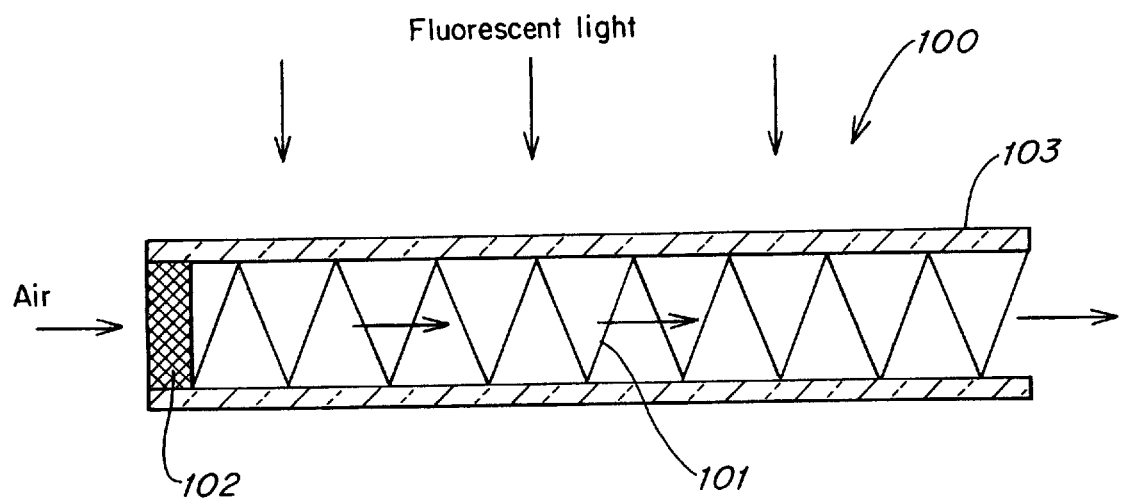
FIGS. 5a–b are illustrations of a chevron-shaped filter employing an LMI coating in accordance with the invention.
Figure 5B:
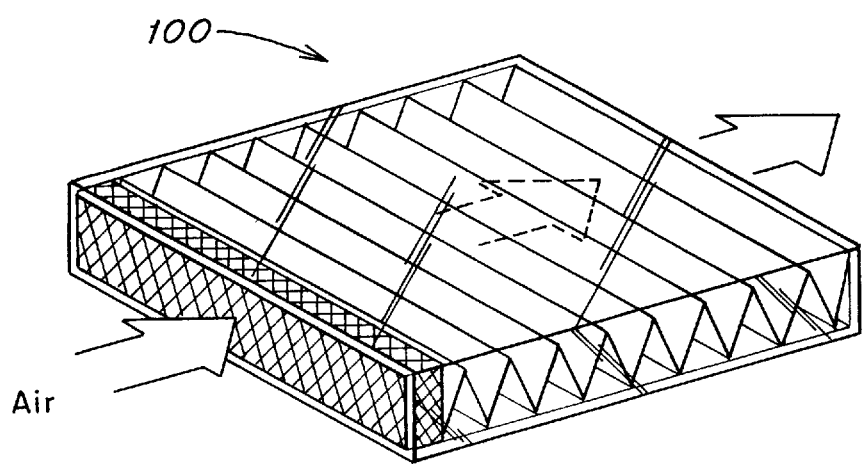

A preferred filter 100 for eradicating airborne bacteria and viruses is illustrated in FIGS. 5a–b and includes an anti-microbial film consisting of separate $TiO_2$+Ag and HAp+Ag layers sprayed onto an electroless silver plated acrylic cloth. The cloth 101 is chevron shaped to enhance the available surface area which contacts the germ bearing gas. A prefilter 102 may be provided to remove gross contaminants such as dust. The prefilter also may include a titania and silver composite film for anti-microbial action. A housing 103, transparent to light at the wavelength of interest (approximately 400 nm for titania), supports the filter. The filter can be placed in vents, ductwork, air conditioning units and other air circulation systems, preferably at the inlet and outlet points. An ordinary fluorescent lamp may be provided where the filter is unlikely to receive adequate lighting.

Figure 6:
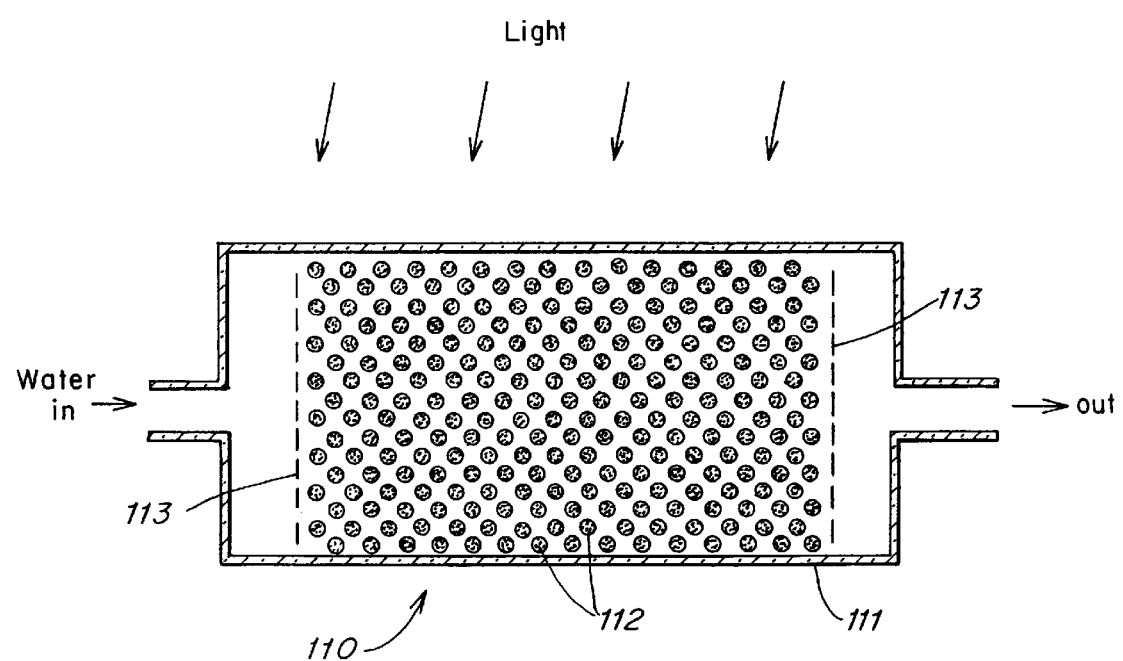
FIG. 6 is an illustration of a filtration column employing ceramic spheres having an anti-microbial coating.

A filter 110 for purifying liquids, such as water, is illustrated in FIG. 6 and includes a column 111 which is transparent to light having a wavelength sufficient to activate a bed of photosemiconductor ceramic balls 112 supported in the body of the column. The ceramic balls may include a porous polycrystalline hydroxyapatite body which is coated with silver (either electroless coated or LMI) and covered by a porous anti-microbial film of titania and silver. Alternatively, the ceramic balls may include a hard alumina spherule which is coated with an LMI hydroxyapatite and silver film. To suppress the growth of algae, nickel or nickel containing metals may be included in the coating or film on the ceramic balls. Preferably, the anti-microbial film includes a combination of silver and nickel conductor metals to combat both algae and bacteria. A prefilter may be positioned at the inlet end of the column to screen out large floating substances and foam. A mesh filter 113, preferably coated with an LMI anti-microbial film, may be provided to support the ceramic beads in the column.

Figure 7:
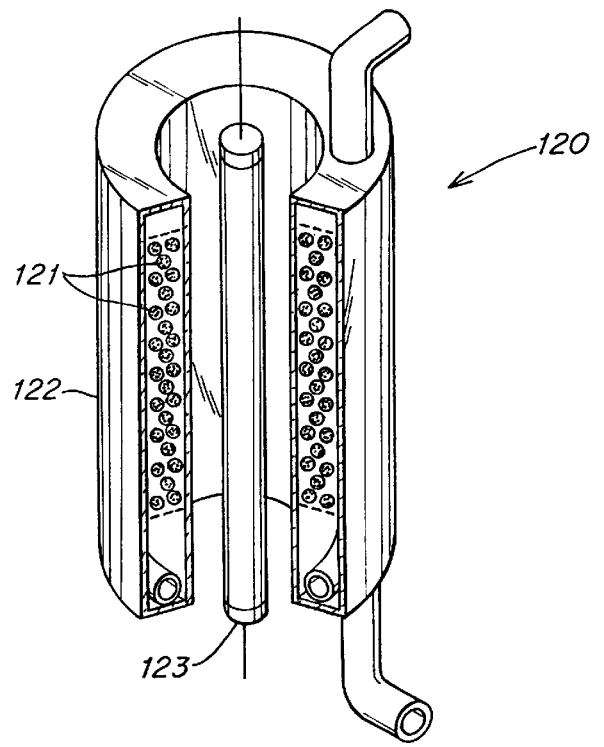
FIG. 7 is an illustration of a system for purifying preconditioned air.
Figure 7:
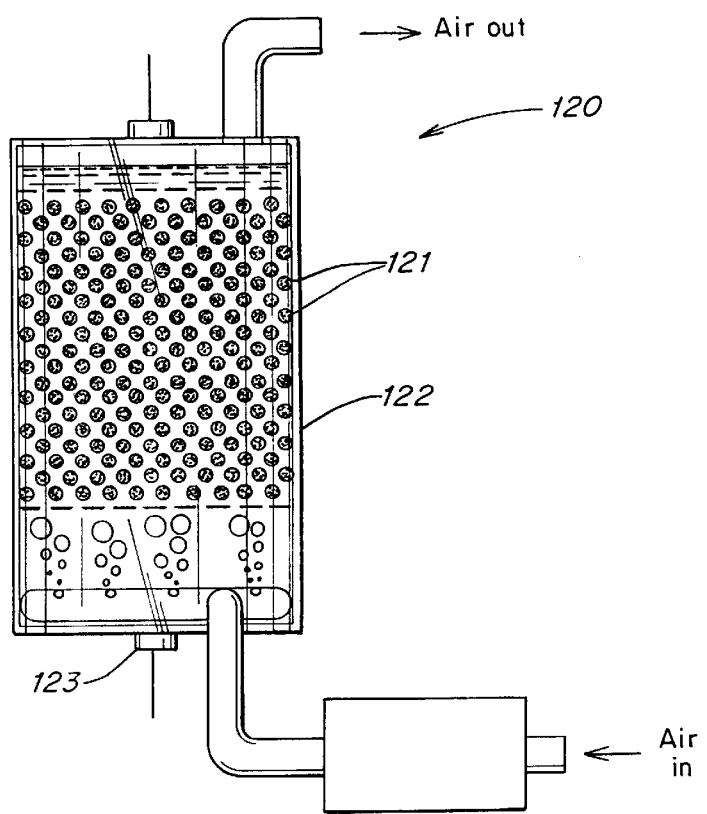

Another filter arrangement 120 is shown in FIG. 7 where conditioned air is compressed and introduced into water as air bubbles. The bubbles rise through the liquid, allowing dust and microbes carried by the bubbles to be absorbed or otherwise transferred to the liquid, cleaning the air. The undesirable microorganisms are eliminated by the sterilizing action of the anti-microbial film coated onto the ceramic balls 121. A filter for the cleansed air bubbles may be provided at the return line to further sterilize the air prior to recirculation back to the air conditioner. An internal fluorescent lamp 123 may be provided to ensure photoactivation, through the UV transparent housing 122, of the anti-microbial film coated on the ceramic balls.

Figure 8:
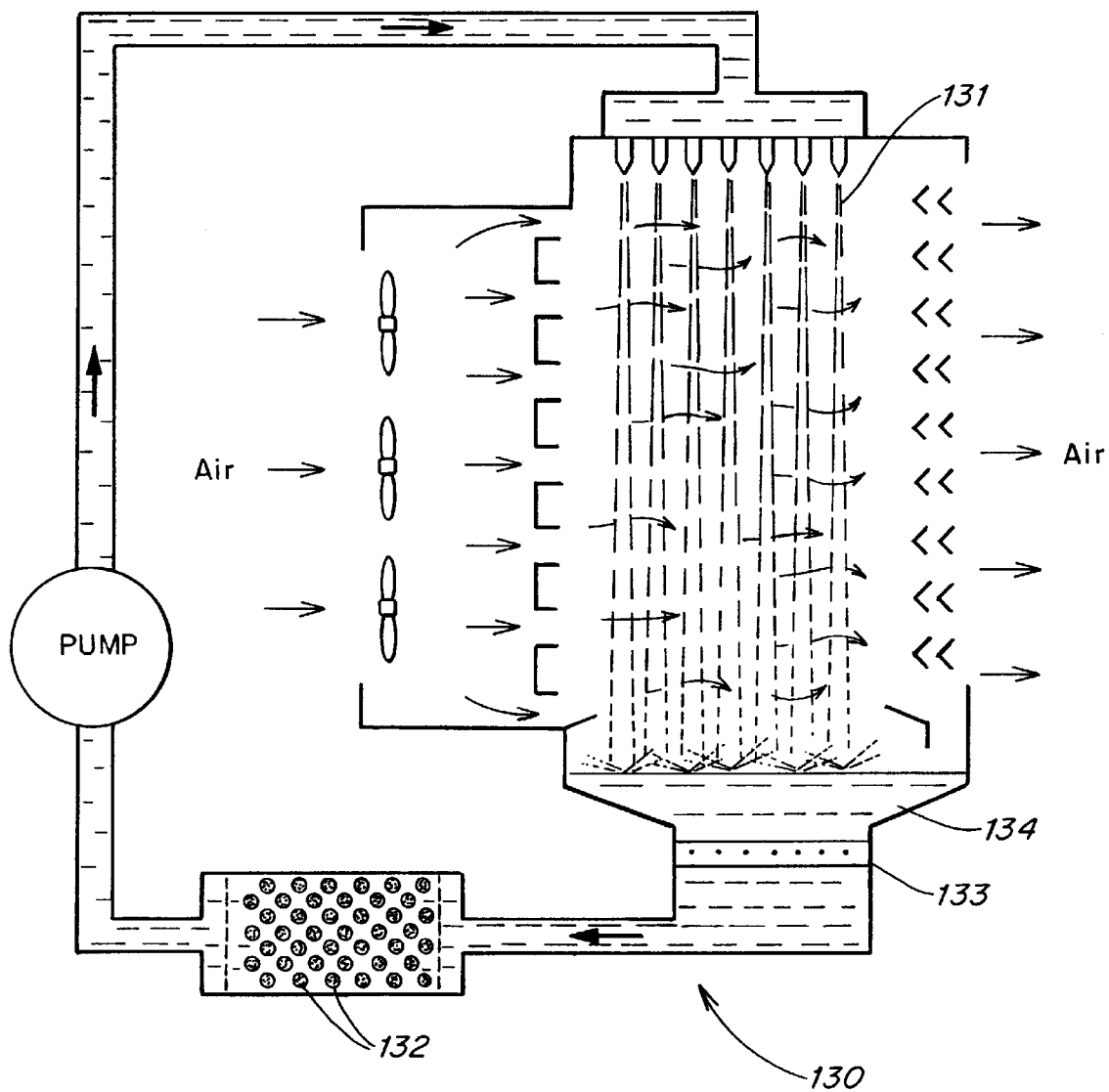
FIG. 8 is an Illustration of a water jet system for purifying air including an anti-microbial filtering column.

FIG. 8 illustrates an air conditioning system 130 which removes air borne dust and microbials in a dense, high pressure water shower 131 which is jetted perpendicular to the air flow. The contaminated water is purified by passing the solution through a sterilization column 132 such as illustrated in FIG. 6. A dust trap 133 may be provided between a water basin 134 and the sterilization column to filter out gross impurities.

Figure 9:
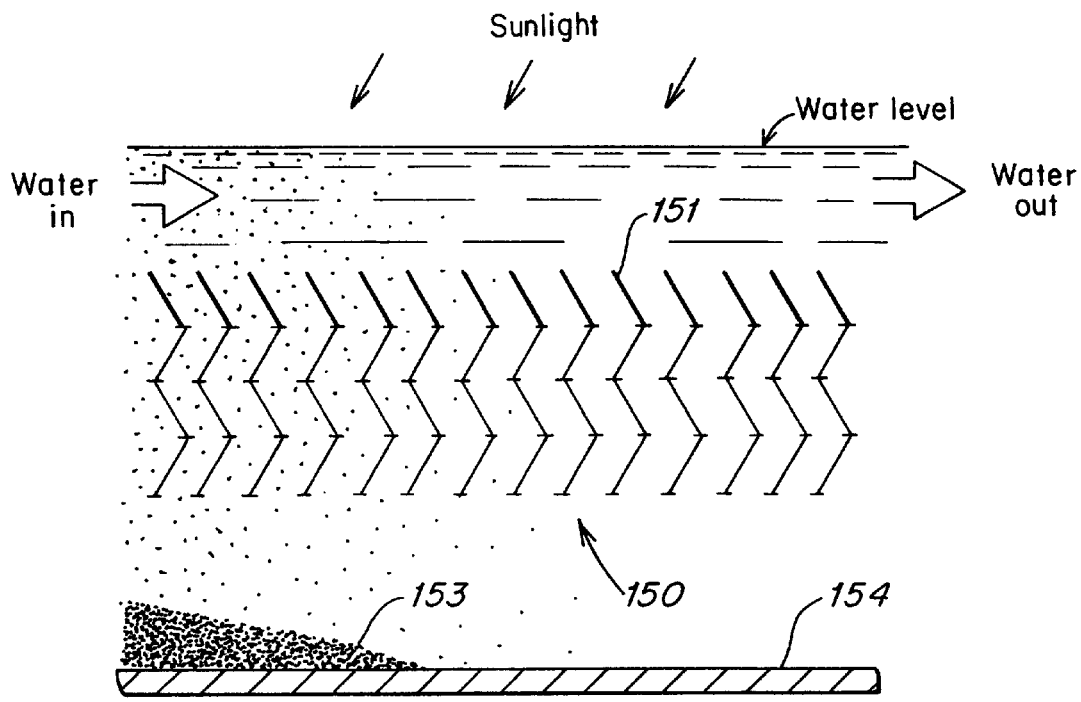
FIG. 9 is a schematic of a water purification system including slant plates coated with an anti-algae film containing nickel conductor particles.

Algae growth in a water purification system may be eliminated by employing a nickel based anti-microbial film as illustrated in FIG. 9. Polyvinyl chloride slant plates 150 typically are provided to promote precipitation of certain substances in the water being treated. Such plates, unfortunately, encourage algae growth particularly on portions of the plate exposed to sunlight. At least those slant plates 151 near the water surface are coated with an anti-microbial film including photosemiconductor and conductor nickel or nickel containing metal particles. Preferably, the slant plate is first coated with nickel and then covered with an LMI $TiO_2$+Ni film. The anti-microbial coating may further include silver and, or in addition, adsorbent particles to eliminate bacteria and other microorganisms in the water. Alternatively, a thin (approximately 0.1 mm) stainless steel foil may be coated with a nickel based LMI film which may then be secured by a water-proof adhesive to the slant plate. The sterilizing agents generated by the electrochemical cell destroy the algae, creating a carcass 153 at the bottom of the tank 151.

A bandage or wound dressing also is contemplated. By bandage is meant any material which can function as a covering for a wound. A wound is meant to include, e.g., damaged skin, burns, cuts, gashes, atopy, diseased skin, and any other condition of the skin in which infection is a possibility. It has been determined, contrary to conventional medical wisdom, that keeping the wound wet or moist is advantageous because the active ions and molecules that are generated on the photosemiconductor and conductor composite surface can migrate through the water to kill microorganisms in the wound.

Accordingly, the bandage preferably includes a flexible water-retaining cloth for directly contacting the wound and conforming to the contours of the skin, tissue or muscle surrounding the wound which is united with a flexible anti-microbial cloth of the present invention. An adsorbent layer may be provided in addition to the photosemiconductor and conductor particulate layer if desired A liquid impermeable polymer layer may be provided over the substrate, forming a reservoir which traps the moisture between the wound and the antimicrobial film, maximizing fluid accumulation. Such a layer also aids in keeping the outer portion of the bandage dry which may come into contact with the clothes of the wearer of the bandage. A moisture vapor impermeable film may be provided over the polymer to prevent evaporation of the fluid. The latter two layers are preferably transparent and may be held together by glue or other means known to those of skill in the art. An additional layer, or a lateral extension of one of the foregoing layers, may be provided with a pressure sensitive adhesive on a backing sheet for releasably sticking the bandage to the skin. It may be preferable to use a moisture impermeable adhesive to assist in retaining water around the anti-microbial film.

Figure 10:
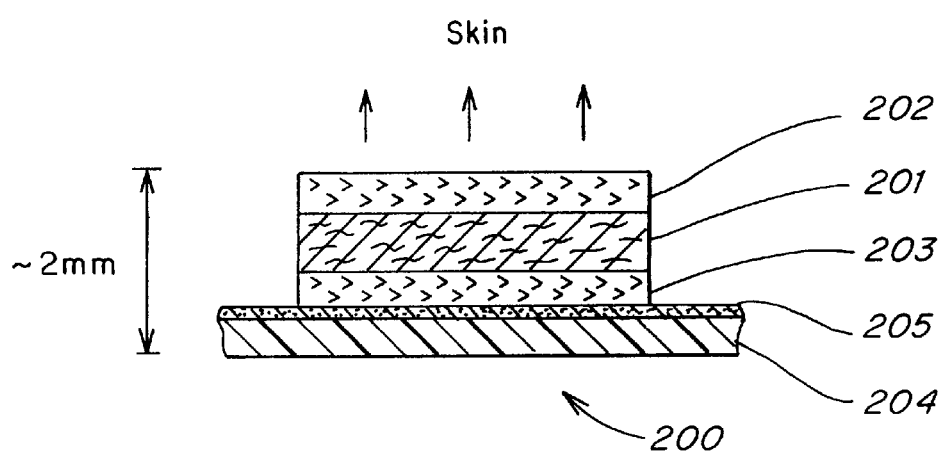
FIG. 10. is a bandage including an LMI film for accelerating wound healing.
Figure 11A:
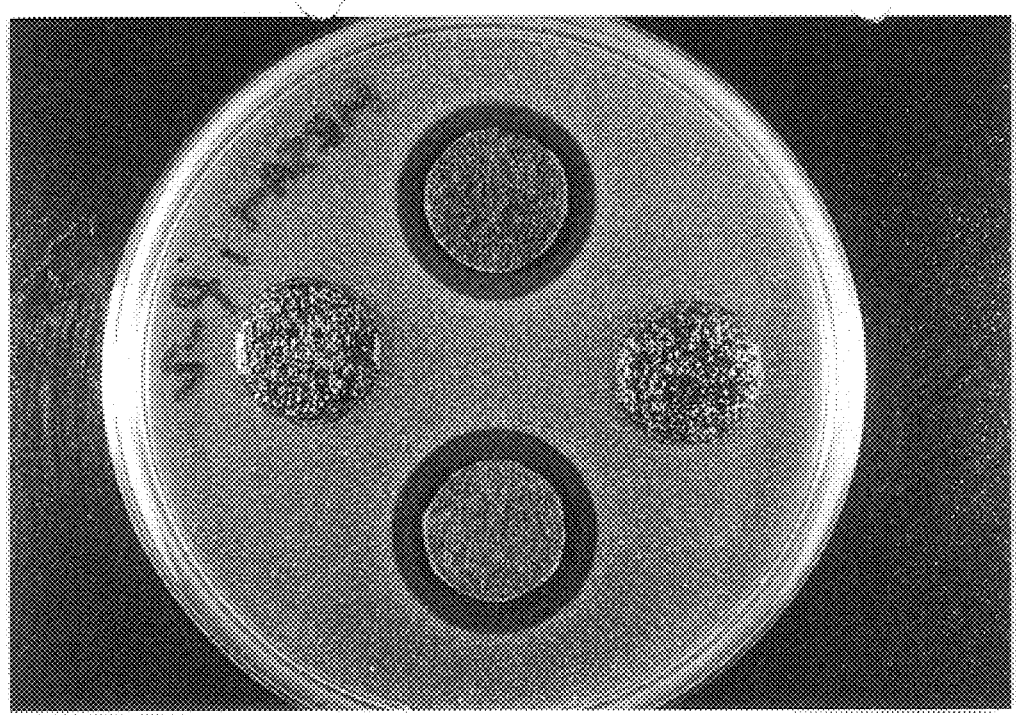
FIGS. 11a–d are photographs of agar samples comparing the sterilizing affect of wet and dry LMI, anti-microbial cloths.
Figure 11B:
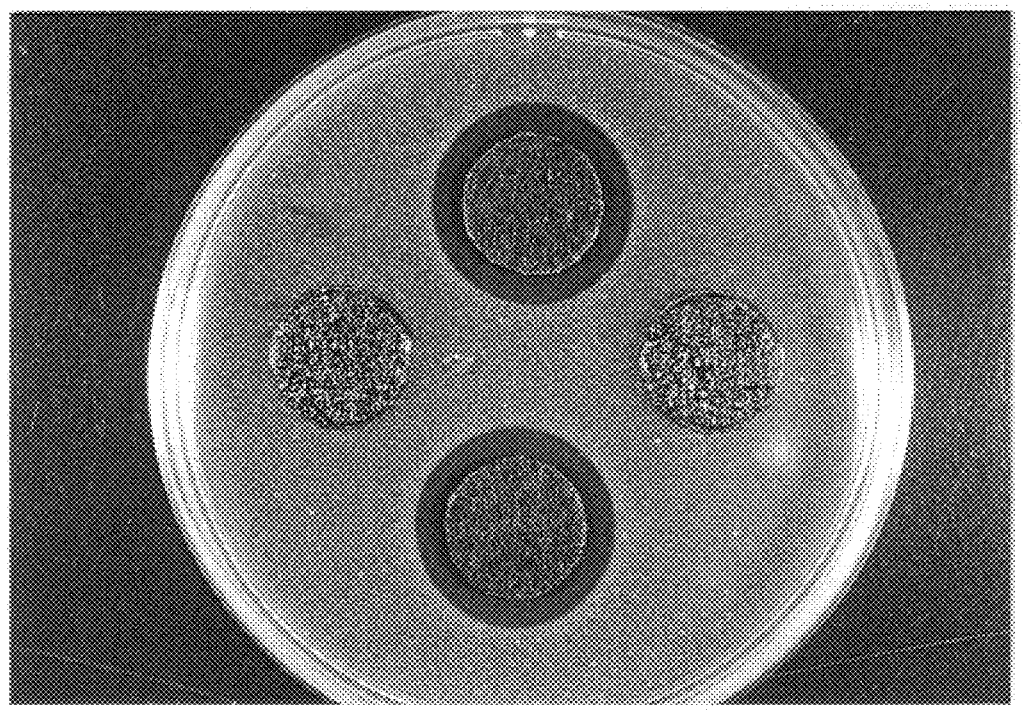
Figure 11C:
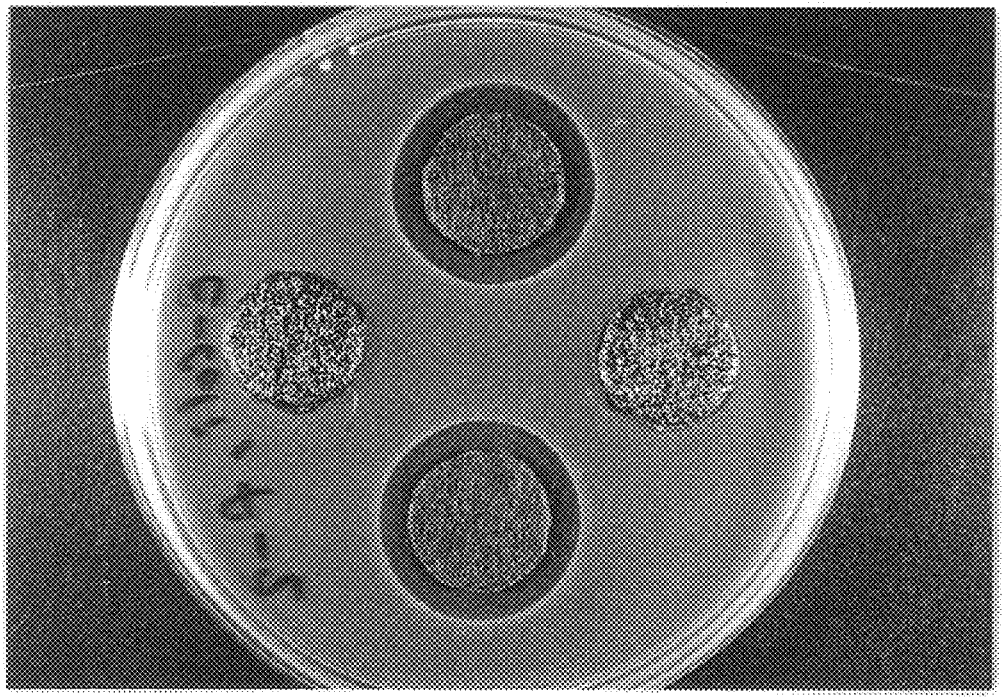
Figure 11D:
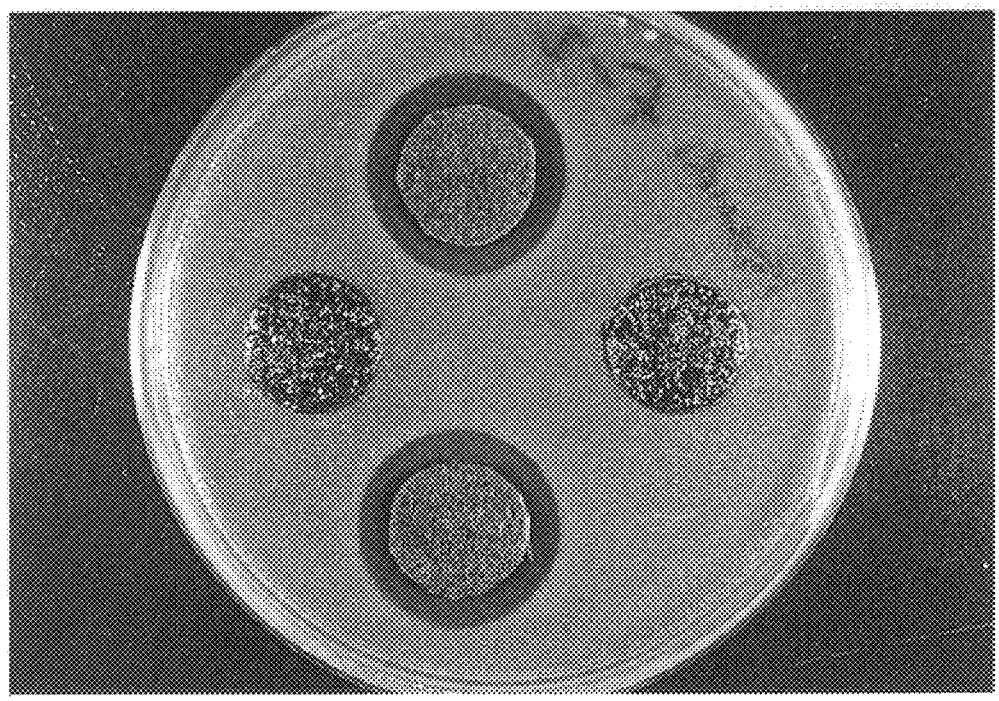
Figure 12A:
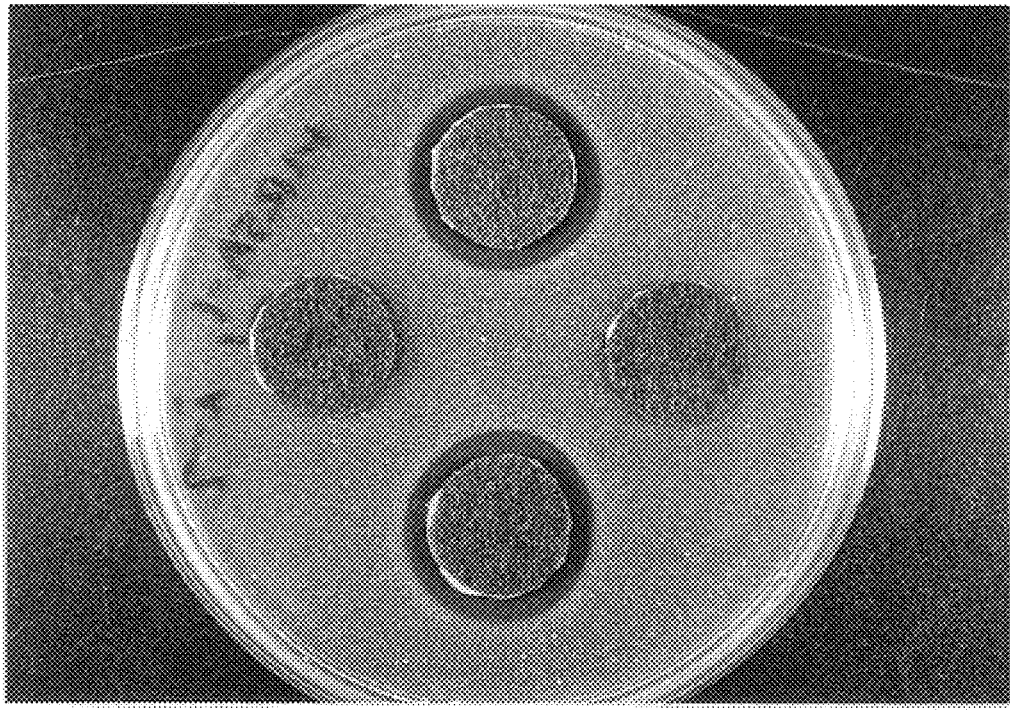
FIGS. 12a–d are photographs of agar samples comparing double layered wet LMI anti-microbial cloths and double Layered wet and dry LMI anti-microbial cloths.
Figure 12B:
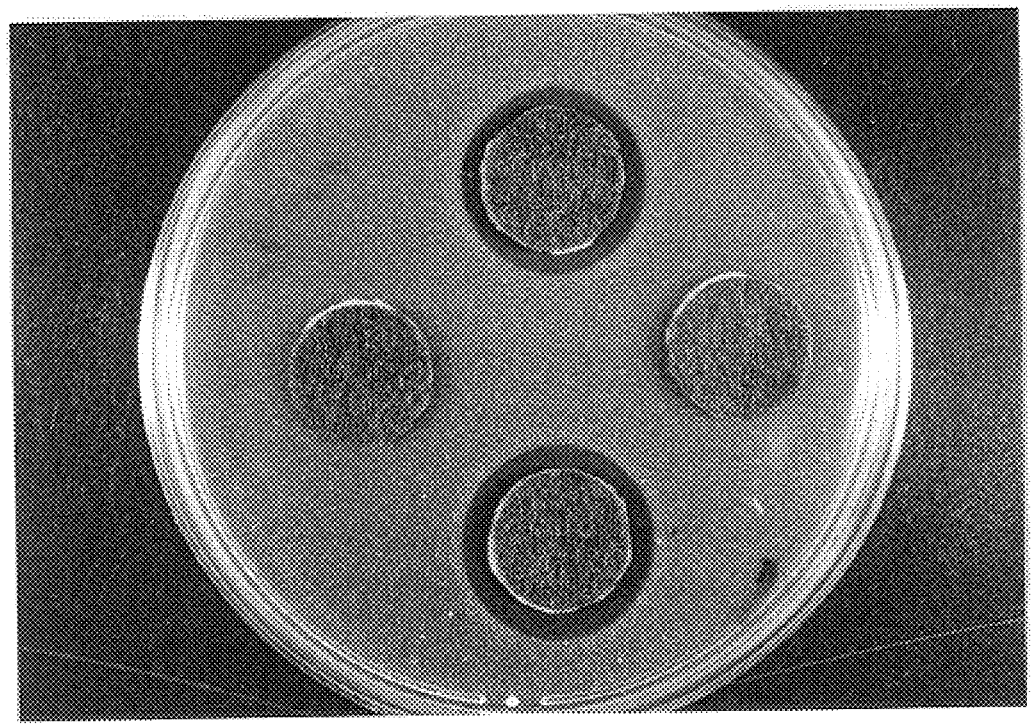
Figure 12C:
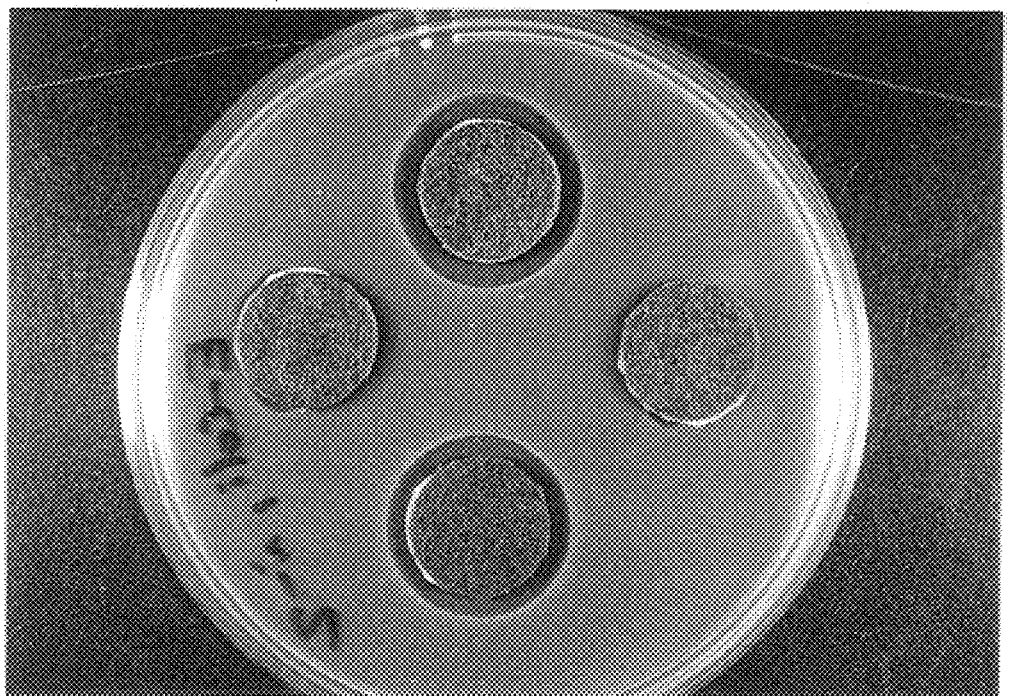
Figure 12D:
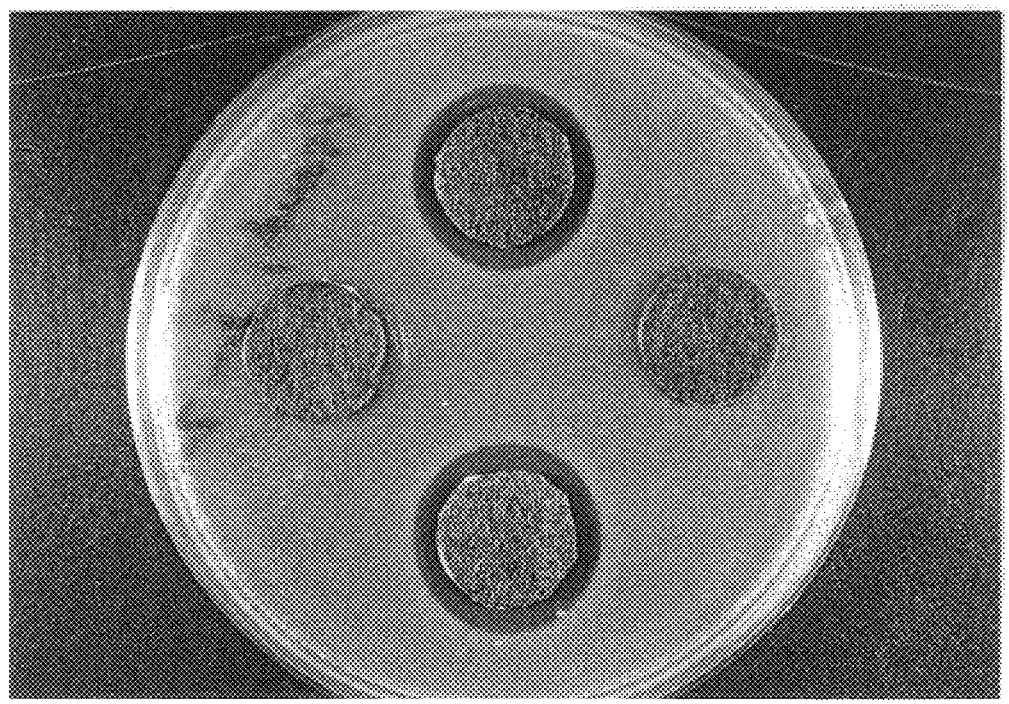

A bandage 200 in accordance with the present invention is illustrated in FIG. 10 and includes an antimicrobial film 201 sandwiched between a pair of water retentive layers 202 and 203. The film 201 preferably includes a dual layer of $TiO_2$+Ag and HAp+Ag which have been coated onto a fibrous substrate, such as the aforementioned polyester and acrylic fabrics or a gauze, that is suitable for overlaying a wound. Care should be taken to ensure that the fabric is inert and atraumatically configured to avoid aggravating the wound. The dual layers may be contiguous or, instead, may include an intermediate zone in which the HAp+Ag and the $TiO_2$+Ag particles coincide. While the bandage may include any combination of the photosemiconductor and conductor materials noted previously, experiments have indicated that the titania and silver pairing has the most favorable sterilizing affect on bacteria. Although a pair of water absorbing sheets are shown, one or more layers would suffice so long as a water pathway is maintained between the anti-microbial film and the source of bacteria. The water retentive sheets may be constructed from artificial fine silk fiber cloths available from Kobayashi Bag Mfg. Co., Ltd. and Siltec Inc. In the embodiment illustrated, layer 202 which directly contacts the wound includes chitosun, a chemical derived from crab shells which has its own anti-microbial affect Chitosun dissolves almost instantly in water allowing anti-microbial action to commence immediately even when the first use of the bandage is in darkness, when the electrochemical cell does not function and the sterilizing affect of silver has yet to become activated. An adhesive layer 205 secures the bandage to the skin, if desired, while moisture vapor and liquid impermeable layer 204 prevents loss of the accumulated fluids by evaporation of leakage. The bandage may be sterilized with UV radiation, or by other techniques as would be apparent to those of skill in the art, prior to packaging.

It is believed that using the above-disclosed bandage will prevent infection of a wound and, or alternatively, facilitate healing of an already infected site by eliminating the presence of bacteria. The bandage is placed in contact with the wound and, preferably, is pre-wetted to encourage formation of the ions and active species believed important in eradicating bacteria. Periodic wetting is advised to ensure that the bandage remains moist. While the bandage will eliminate bacteria even when dry, the sterilizing reach of the anti-microbial film is enhanced dramatically by the presence of water. Indeed, it is believed that moisture generated by the body near the wound, such as perspiration, would enhance the photoreactive affect of the bandage. Here the silk composition of the water retentive layers is especially beneficial as the silk fibers absorb most of the undesirable forms released from the skin including ammonia, carbon dioxide, ethylene and proteins such as putrefactive enzymes. The article may be applied to the skin cutaneously, subcutaneously, by surgery, or may be temporarily or permanently implanted.

The recognition that water enhances the sterilizing affect of the anti-microbial film may be applied to other devices, in addition to the bandage. Thus, it may be beneficial to apply or maintain water around the area or surface being treated. Where the substrate is not water absorbable, a water retentive or vapor absorbable material may be appropriately supplied.

The anti-microbial film and method of applying the film in accordance with the present invention may be considered by reference to the following examples which are intended for purposes of illustration and not by way of limitation.

EXAMPLES

Example 1

Anti-Microbial Properties of Wet Photosemiconductor/Conductor Cloth

This example illustrates that the use of a wet photosemiconductor/conductor cloth has greater antimicrobial properties than a photosemiconductor/conductor cloth which is dry.

Bacteria of a single species were implanted into nutrient broth ('Eiken' Nutrient Broth, #E-MC35), and were left standing overnight to allow for multiplication until their density approached saturation, ~$10^9$ cells per ml. 0.5 ml of this bacterial culture was mixed with 500 ml of sterilized melted nutrient agar ('Eiken' Nutrient Agar, #E-MC01), stirred well, and then poured (~10 ml) into petri dishes. The thickness of the agar layer thus formed was about 2 mm. Three petri dishes (A, B and C) were prepared for MRSA-2 (methicillin resistant Staphylococcus aureus) and two petri dishes (A and B) were prepared for each of MRSA-1, *Escherichia coli* and *Pseudomonas aeruginosa*.

A standard photosemiconductor cloth (Ag-electroless plated acrylic cloth melt-injected with a mixture of TiO2 and Ag) cut in the shape of 17 mm-diameter patches, were prepared in large number. A bare acrylic cloth of the same size was also prepared in large number. Both the standard cloth and bare acrylic cloth were sterilized with UV rays for an hour on both sides. These represented the standard cloth and the bare acrylic cloth under dry conditions. About two dozen pieces of both the standard and bare acrylic dry cloth were soaked in sterilized pure water. These pieces represented the standard cloth and bare acrylic cloth under wet conditions. About a dozen pieces of the dry standard cloth were greased with white vaseline on their surface and sterilized with UV rays. These pieces represented the greased standard cloth.

Immediately after the bacteria-containing agar solidified, the cloth pieces described above were placed on the surface of the agar, and gently tapped on their tops with a sterilized stainless steel tool to ensure good contact between the cloth and the agar.

Two pieces of the wet standard cloth and two pieces of the greased standard cloth were placed, separated from one another, in each of the A petri dishes which contained either MRSA-2, MRSA-1, *Escherichia coli*, or *Pseudomonas aeruginosa*. In each petri dish B, two pairs of double-layered cloth (a wet standard cloth on top of a wet bare acrylic cloth) and two pairs of different double-layered cloth (a wet standard cloth on top of a dry bare acrylic cloth) were deposited. In petri dish C, which was prepared only for MRSA-2, two pieces of the wet standard cloth and two pieces of the dry standard cloth were positioned in similar fashion. These procedures were completed within ten minutes after the agar solidified. All the petri dishes were immediately placed inside an incubator (37° C.) and irradiated overnight with a 30 watt fluorescent lamp (white type) from a distance of 0.4 m.

As shown in FIG. 11, in each of the petri dishes A, a bacteria-free zone or halo was observed around the wet standard photosemiconductor cloth. The boundary between the bacteria-free and bacteria-laden zone was sharp. The volume of the thin cylinder enclosed by this sharp boundary was entirely free of bacteria, and the density of the bacterial colonies outside and near the border was identical to that far from the boundary. The diameter of the haloes was constant for all of the different bacterial species, i.e., 24.4±0.1 mm. In each of the petri dishes A, no bacteria-free zone was observed around and beneath the photosemiconductor cloth which had been greased.

In each of the petri dishes B shown in FIG. 12, a similar bacteria-free zone, except of smaller diameter (22.7±0.1 mm), was observed around the doubled layered, wet standard cloth. There was no bacteria-free halo around the double layered cloth made of the wet photosemiconductor cloth and dry, bare acrylic cloth. Small bacteria-free areas, however, were occasionally observed under the latter cloth. In petri dish C, prepared only for MRSA-2, the interruption volumes were observed around both the wet and dry pieces of the photosemiconductor cloth. The diameter of the halos in the latter (21.4 mm) was smaller than that of the former (24.4 mm). The "dry" cloth in this case was not absolutely dry, because the agar was wet when the pieces of cloth were placed on it.

These results indicate that the sterilization of bacteria is efficient in the presence of water, and that sterilization does not substantially occur without intermediation by water, unless bacteria are in direct contact with the photosemiconductor cloth. The small bacteria-free areas in the agar, that appeared under the double layered, wet/dry cloth, were probably created by local intrusions of water through the generally dry acrylic layer.

Example 2

Mediation, Over a Distance, of Anti-Microbial Properties of Photosemiconductor/Conductor Cloth by Water This example illustrates that water can mediate the anti-microbial effects of a photosemiconductor/conductor cloth when the cloth is not in direct contact with the microbes.

A micro-porous membrane ('Millipore GV,' Japan Millipore, Ltd.—pore size 0.22 $\mu$m) was used to separate bacteria from the photosemiconductor cloth. The space inside the membrane wall of each of three petri dishes, #1, #2, and #3, contained around 10 ml of physiological saline water with MRSA-2 (at a density of ~$10^6$ cells per ml). The outside of the membrane was filled with an aseptic physiological saline water (approximately 35 ml). MRSA is about 1 $\mu$m in size, thus incapable of traveling through the membrane to the other side. Only water molecules, ions, and other molecules smaller than 0.22 pm can transfer through the membrane. In petri dishes #1 and #2, a strip of the standard photosemiconductor cloth surrounded the membrane in a circle (width: 10 mm; circle diameter: 60 mm). In petri dish #2, a finely-woven nickel mesh was additionally installed between the standard cloth and the membrane to provide an electromagnetic shield to the bacteria inside the membrane, in order to determine if the photosemiconductor cloth has an electromagnetic effect on bacteria.

The three petri dishes were placed under the illumination of a fluorescent lamp (15 watt, daylight type) for one hour, at a distance of ~40 cm. Approximately 1 ml was then sampled with a syringe from both the inside and outside of the membrane of each of the three petri dishes, diluted 104 times, and mixed with agar for formation of colonies. Table 1 shows the number/ml of MRSA-2 bacteria in each sample.

TABLE 1

The numbers/ml of MRSA-2 inside (i) and outside (o) of the micro-porous (0.22 $\mu$m) membrane

| | Dish | | | | | |
|---|---|---|---|---|---|---|
| | #1 | | #2 | | #3 | |
| | i | o | i | o | i | o |
| #/ml | $4.8 \times 10^6$ | $<10^3$ | $4.3 \times 10^6$ | $<10^3$ | $8.1 \times 10^6$ | $<10^3$ |

As shown in Table 1, the samples from the outside of the membrane did not contain any bacteria (within the limits of resolution of the experiment), indicating that the MRSA was prevented from being transferred to the other side of the membrane. The number in column 3 represents a "control" since no cloth was included except for the membrane itself. Compared to this number, the concentrations of MRSA-2 from the petri dishes #1 and #2 are considerably smaller.

The results indicate that the MRSA-2 bacteria was sterilized by remote action of the photosemiconductor cloth under illumination. The almost identical results between #1 and #2 also indicate that the sterilization was not made by an electromagnetic field, if the photosemiconductor cloth generated such a field. Apparently, either ions or molecules generated on the surface of the photosemiconductor cloth migrated through the membrane and killed the bacteria, Reactive $OH^-$ and/or $O_2^-$ radicals produced by the photocatalysis may have caused such an effect. Additionally, silver ions generated from the TiO2-Ag film or from the plated silver may have had a sterilization effect. In either case, the presence of water was essential both for generation of those active species and for their transfer to the sterilization region.

The following experiment confirmed the mediation effects of water. The bacteria-containing agar (MRSA-2) was separated from the photosemiconductor cloth by an intervening layer of bacteria-free agar. It is known that bacteria cannot move through agar after the agar has solidified; water molecules, however, can migrate through the agar. Therefore, if the bacteria are still sterilized in this configuration, it would confirm the remote action of sterilization via the water.

Four pieces of the standard photosemiconductor cloth were prepared as above. Two pieces were placed at the bottom of a petri dish prior to pouring in bacteria-free agar. After solidification, the bacteria-free agar was removed from the dish leaving behind two round islands that enclosed the piece of the photosemiconductor cloth. The remaining two photosemiconductor cloth pieces were then placed at the agar-free bottom before filling the dish with bacteria-containing agar (MRSA-2). The experimental conditions were the same as above.

Figure 13A:
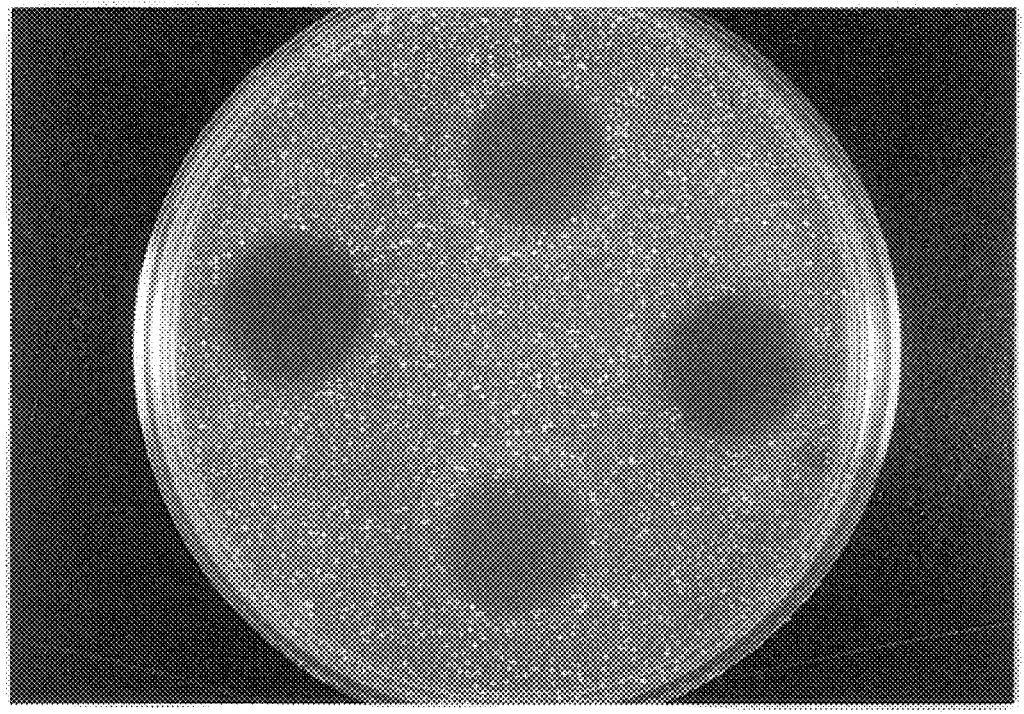
FIGS. 13a–b are photographs of agar samples which confirm the remote sterilizing action of the anti-microbial film through water.
Figure 13B:
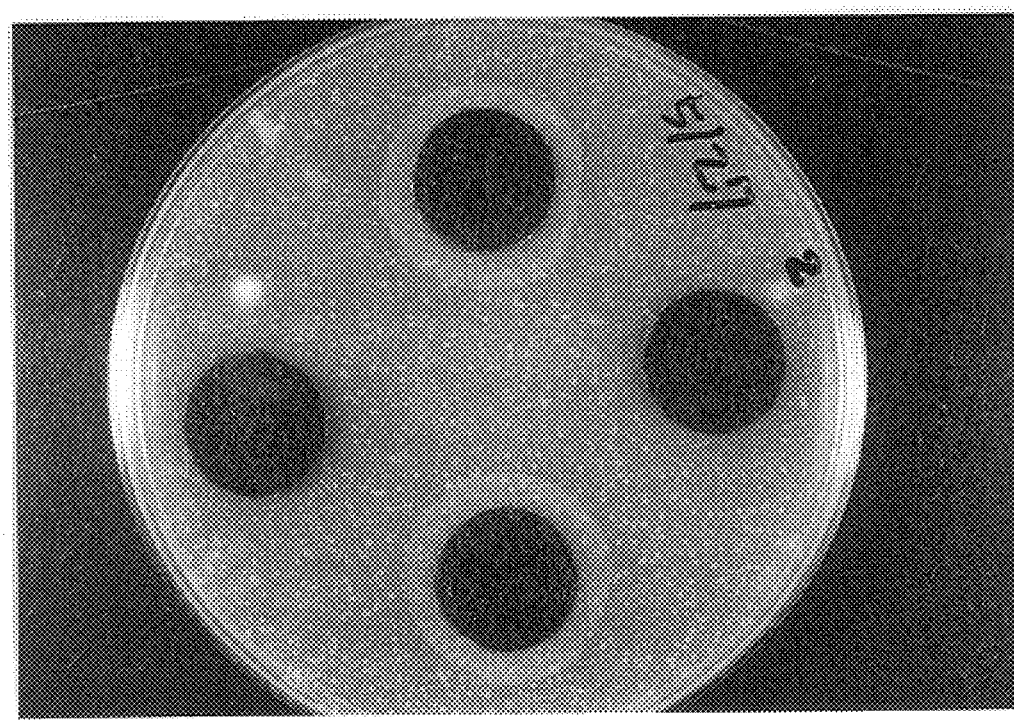

As shown in FIG. 13, round, equally sized interruption areas were formed just above the photosemiconductor cloths, indicating that the bacteria were sterilized through the bacteria-free agar. This evidence confirms the remote action of sterilization via the water.

Example 3

Anti-Microbial Properties of Photosemiconductor/ Conductor Cloth Containing Hydroxyapatite This example illustrates that the presence of hydroxyapatite in a cloth that is coated with a photosemiconductor and conductor composite has greater sterilization properties than a similar cloth without hydroxyapatite.

Sterilization of fluids that are flowing or circulating requires an efficient, quick-effect sterilizer, since the time for interaction between the sterilizing agent and fluids is generally short. A temporary trapping of bacteria and viruses with adsorbents such as hydroxyapatite, zeolite, and activated carbon provides time for the sterilizing agent to effect its sterilizing role.

Hydroxyapatite (HAp) used in this experiment was obtained from the Sekisui Chemical Processing Co., Ltd., Japan. It contains structural water $nH_2O$ in addition to the hydroxyl OH. It has been demonstrated by its manufacturer that this HAp adsorbs viruses very efficiently. Its grain size is ~0.1 $\mu$m when it is precipitated from solution. A further process coagulates it into larger grains of ~10 $\mu$m, which in turn are sintered at low temperatures to mm-sized granules for industrial uses. In the present experiment the granular HAp was crushed gently in a mortar. A fine-grained fraction was washed off with water, leaving the 200–1000 μm size fraction. The latter was dried and sterilized at 190° C. for an hour.

Three samples were prepared in three separate petri dishes. Petri dishes A and B contained 3.5 grams each of the crushed hydroxyapatite (200–1000 μm), spread uniformly at the bottom. Petri dish B additionally contained a round, UV-sterilized, standard photosemiconductor cloth (containing $TiO_2$ and silver) (83 mm in diameter, viz. slightly smaller than the inner diameter of the petri dish) directly over the HAp layer. Petri dish C contained only a round standard photosemiconductor cloth of the same size as in B at the bottom. Petri dishes B and C also contained a small (10×20 mm) piece of the standard cloth.

A detailed structure of the standard photosemiconductor cloth is as follows. It is composed of a base cloth (acrylic unwoven fiber cloth; fibers are ~20 μm in diameter; total thickness of the cloth is ~500 μm), of an electroless plating of Ag (thickness <1 μm; the plating entirely covers the surface of acrylic fiber threads), and of a melt-injection-formed film (~100 μm in thickness) of fine-grained (from 5 to a few tens of μm) mixture of $TiO_2$ and Ag over the surface of Ag-plated fibers.

Physiological saline water containing MRSA-2 ($6.7 \times 10^5$ per ml) was prepared. 10 ml of this solution was poured into dish A, 8.5 ml into dish C, and 18.5 ml into dish B. To prevent multiplication of bacteria during the experiment, the three dishes were half dipped in an ice-water mixture, and were left standing for 20 min. before the first sampling (~1 ml from each dish), and for 90 min. before the second sampling (~1 ml), under the illumination of a 15 watt fluorescent lamp from a distance of 40 cm. The sample solutions were diluted $10^3$ times before being mixed with nutrient agar for colony formation.

The strips of rectangular cloth were immediately removed from the dishes after 90 min., washed thoroughly with bacteria-free saline water in four separate dishes, then dipped into test tubes filled with a nutrient broth ('Eiken' Nutrient Broth, #E-MC35). Small fractions (~0.03 gram) of the HAp were also scooped from dishes A and B immediately after 90 min., washed thoroughly, and dipped into separate test tubes filled with nutrient broth. These test tubes were then kept inside an incubator (37° C.) in order to permit the adsorbed bacteria to multiply. The test tubes were removed from the incubator after four hours, and diluted $10^3$ times before being mixed with nutrient agar for colony formation. This procedure permitted determination of the adsorbed numbers of MRSA-2 in the cloth and HAp grains since the number of MRSA-2 obtained by subtraction of the remaining number from the initial number is the total of both adsorbed and sterilized fractions.

Figure 14:
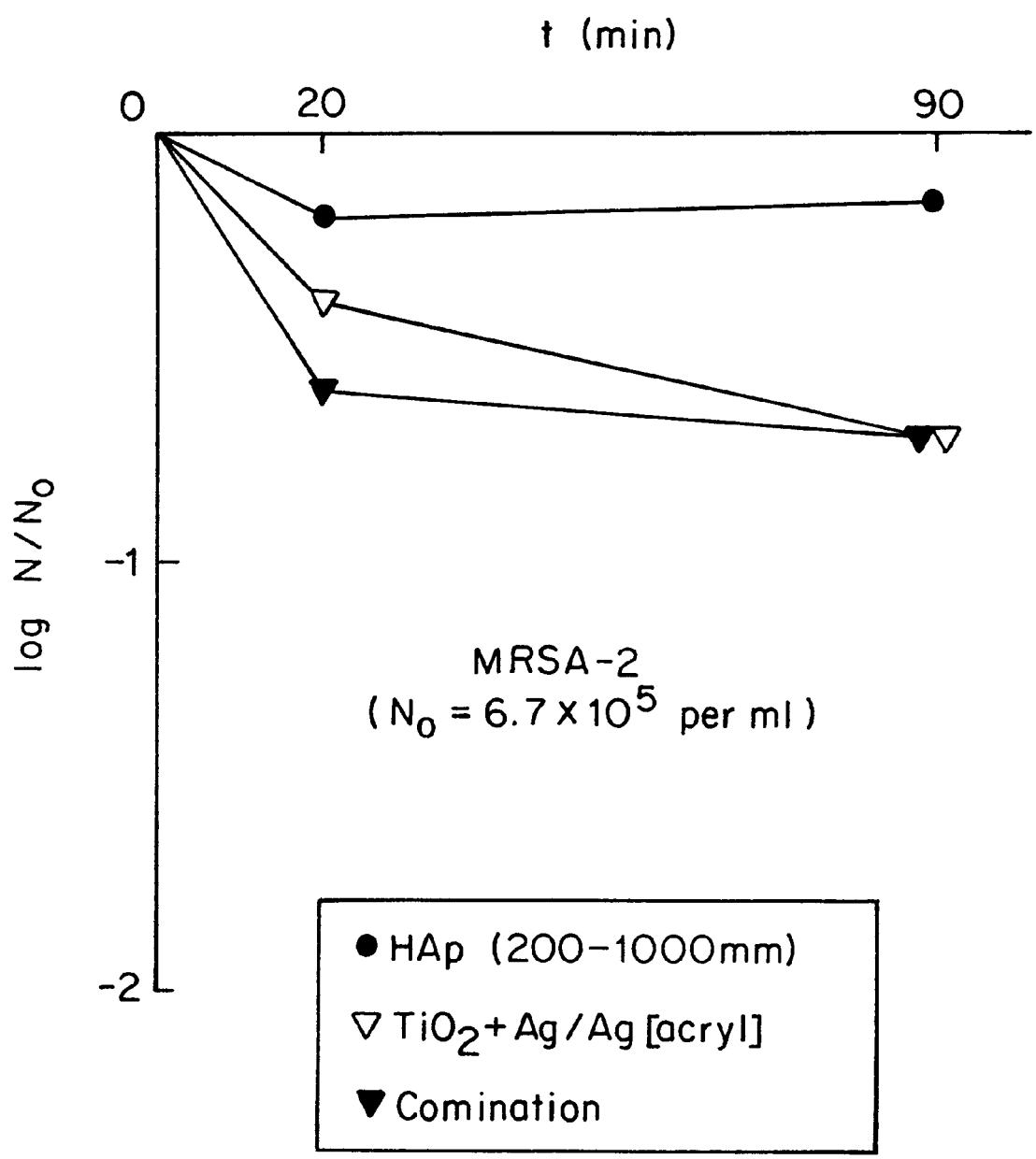
FIG. 14 is a graph slowing viable MRSA-2 bacteria as a function of time after exposure to various cloths with or without hydroxyapatite.

Table 2 and FIG. 14 show the numbers per ml of MRSA-2 bacteria that remained in the saline water, unadsorbed and unsterilized.

TABLE 2

The numbers/ml of MRSA-2* that remained in the saline water after prescribed time durations

| Time | A<br>HAp** | B<br>HAp and SPsC | C<br>SPsC |
|---|---|---|---|
| 20 min | $4.2 \times 10^5$ | $1.7 \times 10^5$ | $2.7 \times 10^5$ |
| 90 min | $4.6 \times 10^5$ | $1.3 \times 10^5$ | $1.3 \times 10^5$ |

*The initial number/ml of MRSA-2 in the saline water at time o ($N_o$) was $6.7 \times 10^5$.
**HAp: hydroxyapatite, 200–1000 μm in grain size. SPsC: standard photosemiconductor cloth, i.e., $TiO_2$ + Ag/Ag[acryl].

Table 3 shows the numbers per ml of MRSA-2 after incubation for four hours.

TABLE 3

The numbers/ml of MRSA-2 after a 4-hour incubation at 37° C.

| | HAp*<br>from A | HAp*<br>from B | Cloth<br>from B | Cloth<br>from C | Control*** |
|---|---|---|---|---|---|
| #/ml | $2.2 \times 10^5$ | $1.3 \times 10^4$ | $\sim 10^2$ | $3.8 \times 10^3$ | $1.7 \times 10^4$ |

*~30 mg of HAp in a test tube.
**A 1 × 2 cm square piece of each cloth in a test tube.
***The initial number/ml of MRSA-2 before incubation was $6.7 \times 10^2$.

The last column of Table 3 represents the number/ml of MRSA-2 after the four hour incubation, whose initial number was $6.7 \times 10^2$/ml. Thus, during incubation, the MRSA-2 bacteria multiplied 25 times. The average duration required for multiplication can be determined as 240×log 2/log 25=52 min. The number of bacteria adsorbed by HAp in dish A is calculated to be $2.9 \times 10^5$ per gram HAp, which corresponds to ~20% of the initial bacteria that existed in the solution at the start of the experiment. This percentage is close to the percentage, ~30%, of the adsorbed and sterilized bacteria relative to the initial number of bacteria, which was derived from the number of remaining bacteria as shown in column 1 of Table 2. Thus it is concluded that HAp adsorbed bacteria, but did not effectively sterilize them.

The number of MRSA-2 bacteria (column 2 of Table 3) that originate from the adsorbed bacteria in the HAp from dish B is significantly smaller than that from dish A (column 1 of Table 2). Apparently most of the adsorbed bacteria in the HAp were sterilized by the action of the photosemiconductor cloth that was present in dish B.

As shown in FIG. 14, the fact that the number of remaining bacteria in dish A did not change between 20 and 90 mins., suggests that the HAp was saturated with bacteria (i.e., the adsorption-desorption equilibrium was reached) in an early phase before 20 min.

The number of remaining bacteria in dish B (which contained both HAp and cloth) is not a simple weighted average of the numbers of remaining bacteria in dish A (which contained only HAp) and in dish C (which contained only the cloth). In fact, the former number is smaller than either of the latter two numbers. This result suggests that adsorption and sterilization are not separate parallel processes, but are positively coupled. A simple interpretation for this is that remote action of sterilization via water, as shown in the previous Examples, worked on the bacteria that were adsorbed on the surface of the HAp grains, and replenished adsorption sites so that more bacteria could be caught by the HAp.

As the number of bacteria in the solution diminish, the adsorbing capacity is reduced according to the Langmuir's adsorption isotherm theory. Thus, it is predicted that the positive coupling becomes less effective with time. It is likely that at a certain point the sterilization rate of the bacteria becomes controlled by the desorption kinetics of the bacteria from the surface of HAp, which is presumably sluggish.

Example 4

Microbial Adsorption Properties Of Photosemiconductor/Conductor Cloth Containing Hydroxyapatite This example illustrates that a layer of hydroxyapatite+ silver on a silver plated cloth results in significant adsorption and sterilization of microbes. If the hydroxyapatite is mixed with $TiO_2$ and Ag, and simultaneously melt-injected over the surface of Ag-plated acrylic fiber cloth, the high temperature (>1850° C.) required to melt $TiO_2$ will destroy the effectiveness of the hydroxyapatite, by forming an anhydrous amorphous phase which has no adsorption power. The hydroxyapatite which possesses a strong adsorption capability contains structural water $nH_2O$, which is easily removed from the crystal structure upon heating over 1000° C. Hydroxyapatite, particularly with $nH_2O$, is so susceptible to heat that it is not possible to effectively melt-inject it onto the base cloth.

Admixing a binding material, such as epoxy, to hold the hydroxyapatite grains on the surface of the cloth results in very small adsorption capability because most of the effective surface area of the hydroxyapatite is covered with the binding material.

This Example attaches hydroxyapatite grains to a cloth without using any binder. The mixture of 90 wt % of HAp (35 μm in average grain size) and 10 wt % of Ag grains was injected onto the Ag electroless plated cloth at ~1000° C., slightly above the melting point of metallic silver. At this temperature, HAp neither melts nor decomposes; Ag melts. The molten Ag binds the HAp grains to the acrylic fibers, giving sufficient structural support to the HAp grains. As a result of this low-temperature melt injection, the formed layer is porous, in ~10 μm scales. Additionally, Ag has a sterilization effect by itself.

Five different test materials were used: (i) a HAp+Ag injection layer over a Ag-plated acrylic cloth (hereafter HAp+Ag/Ag[acrylic]), prepared as described above; (ii) a bare acrylic fiber cloth; (iii) pure HAp grains (100–500 μm in grain size); (iv) an Ag-plated acrylic cloth; and (v) the standard photosemiconducting cloth. The test materials were prepared in separate petri dishes, onto which 7 ml each (10 ml for the petri dish that contained only HAp grains) of physiological saline water that contained MRSA-2 bacteria ($6 \times 10^5$ per ml) was poured. The sizes of the various cloth pieces, the total weight of the HAp grains, and the illumination condition were identical to those described in Example 1. Similarly, small strips (1×1 cm) of the same cloth were included in the dishes to determine multiplication values. 0.4 ml of saline was sampled from each petri dish at 6 (or 8) min, 14 (or 17) min, and 45 min after the onset of the experiment. An additional sampling was made from the petri dish that contained the HAp+Ap/Ag[acrylic] cloth at 130 min after the onset. The samples were diluted $10^3$ times before being mixed with nutrient agar, and were incubated overnight for colony formation. The small strips of cloth and a sample of HAp were taken at 130 min, washed thoroughly, dipped into test tubes containing nutrient broth, and incubated (37° C.) for four hours. The samples were then diluted $10^2$ times with broth before being mixed with nutrient agar and incubated overnight.

Figure 15:
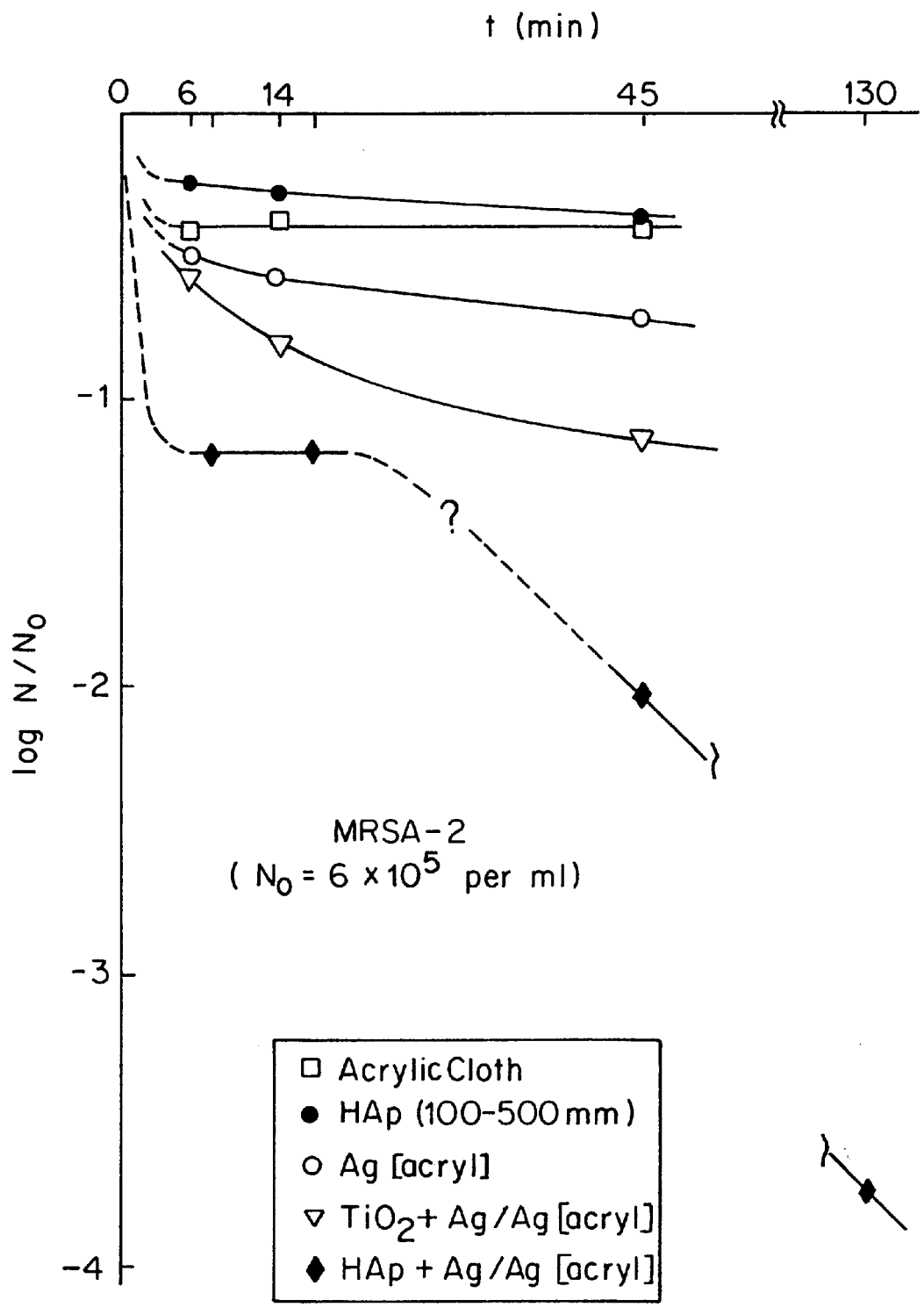
FIG. 15 is a graph showing viable MRSA-2 bacteria as a function of time after exposure to various cloths with or without a melt injected layer of hydroxyapatite and silver.

The results are shown in Table 4 and FIG. 15.

TABLE 4

The numbers/ml of MRSA-2* that remained in the saline water after prescribed time durations (in minutes), and the numbers/ml of MRSA-2 after a 240 minute incubation at 37° C.

| Time | Acrylic cloth** | HAp (100–500 um) | Ag [acryl] | $TiO_2$ + Ag/ Ag [acryl] | HAp + Ag/ Ag [acryl] | |
|---|---|---|---|---|---|---|
| 6 | $2.3 \times 10^5$ | $3.5 \times 10^5$ | $1.9 \times 10^5$ | $1.6 \times 10^5$ | — | |
| 8 | — | — | — | — | $3.8 \times 10^4$ | |
| 14 | $2.5 \times 10^5$ | $3.2 \times 10^5$ | $1.6 \times 10^5$ | $9.2 \times 10^4$ | — | |
| 17 | — | — | — | — | $3.9 \times 10^4$ | |
| 45 | $2.3 \times 10^5$ | $2.4 \times 10^5$ | $1.1 \times 10^5$ | $4.2 \times 10^4$ | $5.3 \times 10^3$ | |
| 130 | — | — | — | — | $\leq 10^2$ | |
| 240 | $7.0 \times 10^2$ | $4.9 \times 10^4$ | ~10 | $1.8 \times 10^2$ | ~10 | $4.5 \times 10^{4***}$ (control) |

*The initial number/ml of MRSA-2 in the saline water at time 0 ($N_0$) was $5.9 \times 10^5$.
**A 1 × 1 cm square piece of each cloth in a test tube; ~30 mg of HAp in a test tube
***The initial number/ml of MRSA-2 before incubation was $6 \times 10^3$.

As described in Example 1 the number of bacteria inside the test tube that contained HAp was reduced to the initial number of bacteria before the incubation, confirming the adsorbed+sterilized fraction of bacteria that existed in the HAp-containing dish was in fact represented by the adsorbed ones. No bacteria were detected from the test tubes that contained the HAp+Ag/Ag[acrylic] cloth after incubation, suggesting either that no live bacteria remained adsorbed after the long duration (130 min) of the experiment, or alternatively, a small number of adsorbed, live bacteria on the cloth were further sterilized by the action of the Ag during the incubation. The bare acrylic cloth kept some bacteria adsorbed even after the repeated wash of the cloth before incubation.

FIG. 15 demonstrates that the time constant of the adsorption process by the HAp grains is less than 6 min. In this experiment, however, HAp demonstrated a gradual increase of adsorbing capacity with time.

The bare acrylic cloth also showed a significant adsorption at the early stage in less than 6 min. However, this adsorption is apparently very weak. As was done for the HAp grains, the number of the adsorbed bacteria by the bare acrylic cloth can be calculated from the number after incubation, which was only 1/100 of the total bacteria that were initially present in the petri dish. On the other hand, only 40% of the initial bacteria remained in the saline water, indicating that 60% of the bacteria were adsorbed by the cloth. Apparently most of the adsorbed bacteria were washed off during the four washing steps of the cloth strips taken before being dipped into the nutrient broth in the test tubes.

This weak adsorption is in stark contrast with the strong binding of bacteria with HAp, which was not significantly affected during the washing steps described above. Such a strong adsorption exerted by HAp suggests that the adsorption observed in the present experiments was controlled by chemisorption at the reactive sites, such as the OH bases, rather than by a simple trapping of bacteria within cavities present in HAp. The modal size of these cavities in the HAp provided by the Sekisui Chemical Processing Co. Ltd. is presumably submicron because the initial grain size before the coagulation was ~0.1 $\mu$m. Such micro-cavities would be most appropriate for trapping viruses whose sizes are far smaller than those of bacteria.

The decreases of MRSA-2 bacteria in the saline water with time, as observed for the Ag[acrylic] cloth and the $TiO_2$+Ag/Ag[acrylic] cloth, were caused by the sterilization of the bacteria by the silver ions and with the photosemiconductor-conductor photocatalysis. The most remarkable feature revealed in this experiment is that the HAp+Ag/Ag[acrylic] cloth showed a far stronger adsorption-sterilization coupling. Clearly, the HAp grains on the surface of the cloth were very effective as indicated by the large dip of the log $N/N_0$ value within 6 min, as shown in FIG. 15. The flat feature of the curve during 6 to 17 min suggests that the HAp became temporarily saturated with bacteria. The big drop that follows this phase suggests a recovery of available adsorption sites. Such a feature may be explained by the sterilizing characteristics of silver ions. It is known that it usually takes a significant period of time for silver ions to initiate their sterilizing action because bacteria die only after incorporating these ions into their cells. In the present experiments, such actions apparently became significant ~20 min after the cloth was dipped into the bacteria-laden saline water.

The inclination of the curve for the HAp+Ag/Ag[acrylic] cloth starting at 20 min, is larger than for the other two cloths. It is likely that this highly efficient adsorption-sterilization coupling comes from the geometric supremacy of the HAp+Ag film. The low-temperature melt injection technique creates innumerable, microscopic direct contacts between the injected ingredients, and between these ingredients and the Ag plated fibers, without interruption by other materials such as epoxy resins. Furthermore, the film formed is highly porous, allowing easy infiltration of liquid into the structure. The outcome of these advantages is that the adsorption sites are infinitely close to the sites where sterilization is most effectively made (Ag grains and Ag plating in this example). The anticipated effect is a fast "trap and kill" process with almost no delay between these two steps. As a result, the available adsorption sites increase, which in turn enhances the adsorption rate according to the Langmuir adsorption isotherm theory. Ideally, the rate of sterilization can be increased up to the intrinsic rate of adsorption, which is controlled only by the adsorption kinetics.

Example 5

Configuration of Photosemiconductor/Conductor Cloth Which Shows Strong Microbial Adsorption and Sterilization Properties This example illustrates a preferred layered configuration of photosemiconductor/conductor cloth such that the cloth exhibits strong microbial adsorption and sterilization properties. The specific geometry of the adsorption and sterilization layers is important in the creation of efficient adsorption-sterilization materials.

A drawback of using silver in sterilization filters is that its sterilization function is not immediate, but generally requires about 20 min to be effective. Since bacterial or virus-laden fluids (air or water) pass through filters continuously, a quick sterilization effect is required.

Three types of melt injection-formed cloth were tested: the $TiO_2$+Ag/HAp+Ag/Ag[acrylic] cloth (viz. the $TiO_2$+Ag layer on top of the HAp+Ag layer), the HAp+Ag/Ag [acrylic] cloth, and the standard $TiO_2$+Ag/Ag[acrylic] cloth.

A round-shaped (83 mm diameter) piece of each of these cloths was placed into the bottom of separate petri dishes (three petri dishes altogether). One empty dish was prepared as a control. 6 ml of physiological saline water which contained MRSA-2 (1.7×10 per ml) was poured (time zero) into each dish; these petri dishes (with no covers) were kept irradiated from the top with a 15 watt fluorescent lamp (daylight type). The saline water was sampled from each dish at 5, 15 and 45 mins after the onset of the experiment, diluted $10^3$ with broth, mixed with nutrient agar, and incubated overnight for formation of colonies.

Another set of four petri dishes were prepared for a similar test using *Pseudomonas aeruginosa* (1.8×$10^6$ per ml). The experimental conditions and procedures were identical to those described above.

Figure 16:
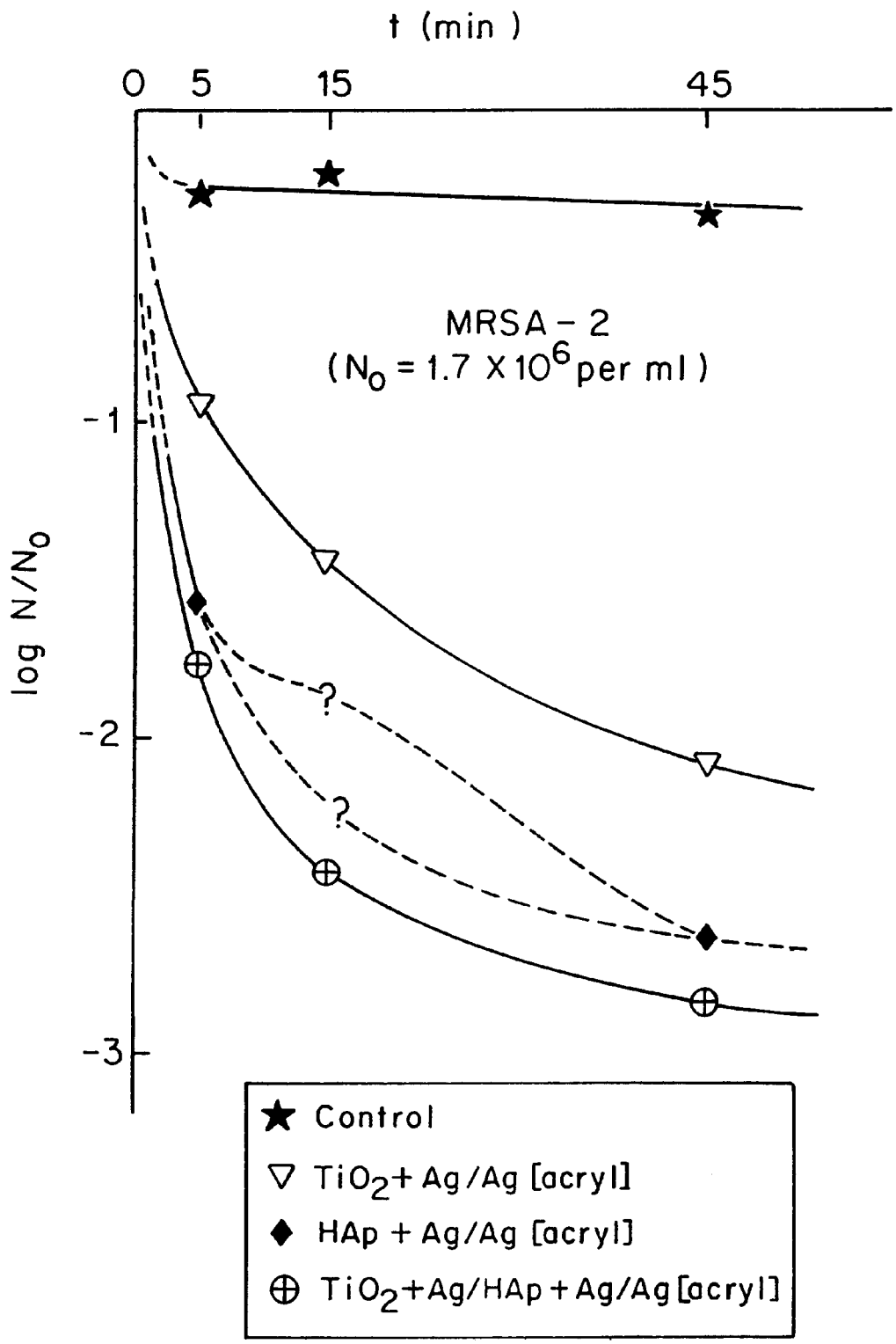
FIG. 16 is a graph showing viable MRSA-2 bacteria as a function of time after exposure to various cloths with or without a melt injected layer of hydroxyapatite and silver.
Figure 17:
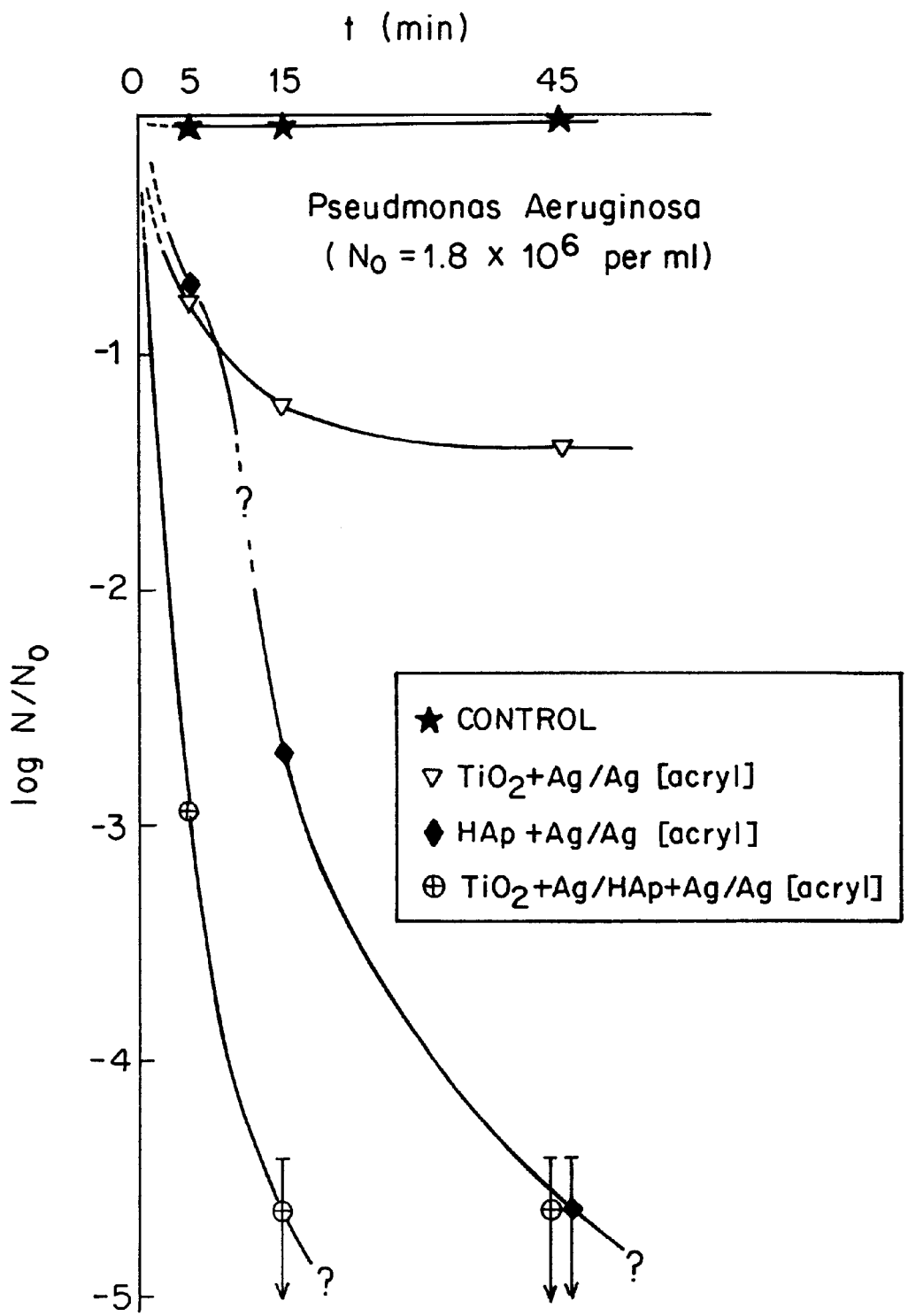
FIG. 17 is a graph snowing viable *Pseudomonas aeruginosa* bacteria as a function of time after exposure to various cloths with or without a melt injected layer of hydroxyapatite and silver.

The results are shown in Table 5 and FIGS. 16 and 17.

TABLE 5

The numbers/ml of MRSA-2 and *Pseudomonas aeruyinosa* that remained in the saline water after prescribed time durations.

| | MRSA-2* | | | |
|---|---|---|---|---|
| Time | 1*** | 2 | 3 | control |
| 5 min | $1.9 \times 10^5$ | $4.4 \times 10^4$ | $2.8 \times 10^4$ | $8.8 \times 10^5$ |
| 15 min | $6.1 \times 10^4$ | — | $6.2 \times 10^3$ | $1.0 \times 10^6$ |
| 45 min | $1.3 \times 10^4$ | $3.7 \times 10^3$ | $2.3 \times 10^3$ | $7.2 \times 10^5$ |

| | *Pseudomonas aeruginosa*** | | | |
|---|---|---|---|---|
| Time | 1 | 2 | 3 | control |
| 5 min | $3.0 \times 10^5$ | $3.5 \times 10^5$ | $2.1 \times 10^3$ | $1.6 \times 10^6$ |
| 15 min | $1.1 \times 10^5$ | $3.7 \times 10^3$ | $\leq 4 \times 10^1$ | $1.7 \times 10^6$ |
| 45 min | $7.0 \times 10^4$ | $\leq 4 \times 10^1$ | $\leq 4 \times 10^1$ | $1.8 \times 10^6$ |

*The initial number/ml of MRSA-2($N_0$) was $1.7 \times 10^6$.
**The initial number/ml of Pseudomonas aeruginosa ($N_0$) was $1.8 \times 10^6$.
***Cloth 1: $TiO_2$ + Ag/Ag[acryl]
Cloth 2: HAp + Ag/Ag[acryl]
Cloth 3: $TiO_2$ + Ag/HAp + Ag/Ag[acryl]
control: no cloth Both for MRSA-2 and *Pseudomonas aeruginosa*, the $TiO_2$+Ag/HAp+Ag/Ag[acrylic] cloth showed the best adsorption-sterilization coupling. It did not show any plateau or saturation feature in the early stage, in contrast with the HAp+Ag/Ag[acrylic] cloth. A saturation feature for the HAp+Ag/Ag[acrylic] cloth for *Pseudomonas aeruginosa* appears to exist.

By comparing the results of the standard $TiO_2$+Ag/Ag [acrylic] cloth with that of the $TiO_2$+Ag/HAp+Ag/Ag [acrylic] cloth, the effect of the adsorption layer is evident. The coupling between the adsorption and sterilization, as exhibited by the latter configuration, enhances the overall sterilization efficiency by $10-10^4$ times. The apparent absence of a saturation feature for this cloth suggests that the $TiO_2$+Ag electrochemical cells predominate in effecting sterilization, as compared to the silver alone. In addition, the "trap and kill" mechanism suggested for the HAp+Ag/Ag [acrylic] is also apparently functioning in this configuration because the low-temperature melt injection creates intimately mixed zones of the underlying and overlying layers due to their porous and fine-grained nature, viz. many HAp grains sit side by side with $TiO_2$ and Ag in the mixed zones.

Example 6

Anti-Microbial Film Containing Nickel Suppresses Growth of Algae

These experiments indicate that a $TiO_2$+Ni film can be an invaluable weapon in growth control and eradication of algae. This effect is far stronger for films containing nickel or nickel containing alloys than for $TiO_2$+Ag combinations which are more effective in the sterilization of other microbials such as bacteria, viruses, and fungi. These results suggests that different photosemiconductor-metal pairs create different kinds of growth suppression and sterilization effects. Thus, a parallel-coupled configuration of such different pairs or a simple mixing of various photosemiconductors and metals in one composite film will generate multi-purpose growth controls and sterilizations.

Experiment 1

1 mg/liter of ammonium hydroxide, 0.1 mg/liter of phosphoric acid, and 5 ml of algae planted solution were added to two similar basins filled with 35 liters of water. Air was continuously pumped into the water. Two pieces (7"×5.5") of Ni-plated polyester cloth coated with an LMI $TiO_2$+Ag film were immersed completely under water in Basin A. Basin B did not contain any anti-microbial cloth. The water temperature was kept at 19° C.

The experiment continued for 44 days without any water exchange. The inside walls of Basin A stayed free of algae, while those of Basin B were fully covered with algae. Table 6 shows pH values and concentrations of nitric and nitrous acids in the water at the start (Day 0) and after 44 days (pH was not measured). At the outset, the two sets of these values are identical within errors After 44 days, however, neither nitric nor nitrous acid was detected in the water in Basin B. The concentrations of these acids are virtually unchanged for Basin A after 44 days. It seems clear that the algae grew in Basin B by photosynthesis that consumed nitric and nitrous oxides in water.

TABLE 6

The pH and Concentrations of Nitric and Nitrous Oxide Ions

| | Start (Day 0) | | Day 44 | |
|---|---|---|---|---|
| | Basin A (with cloth)* | Basin B (no cloth) | Basin A (with cloth) | Basin B (no cloth) |
| pH | 7.1 | 7.2 | — | — |
| $NO_3$— | 1.30** | 1.25 | 1.33 | 0.00 |
| $NO_2$— | 0.02** | 0.02 | 0.03 | 0.00 |

*Photosemiconductor cloth is $TiO_2$ + Ag/Ni[polyester].
**mg/l

Experiment 2

Figure 18:
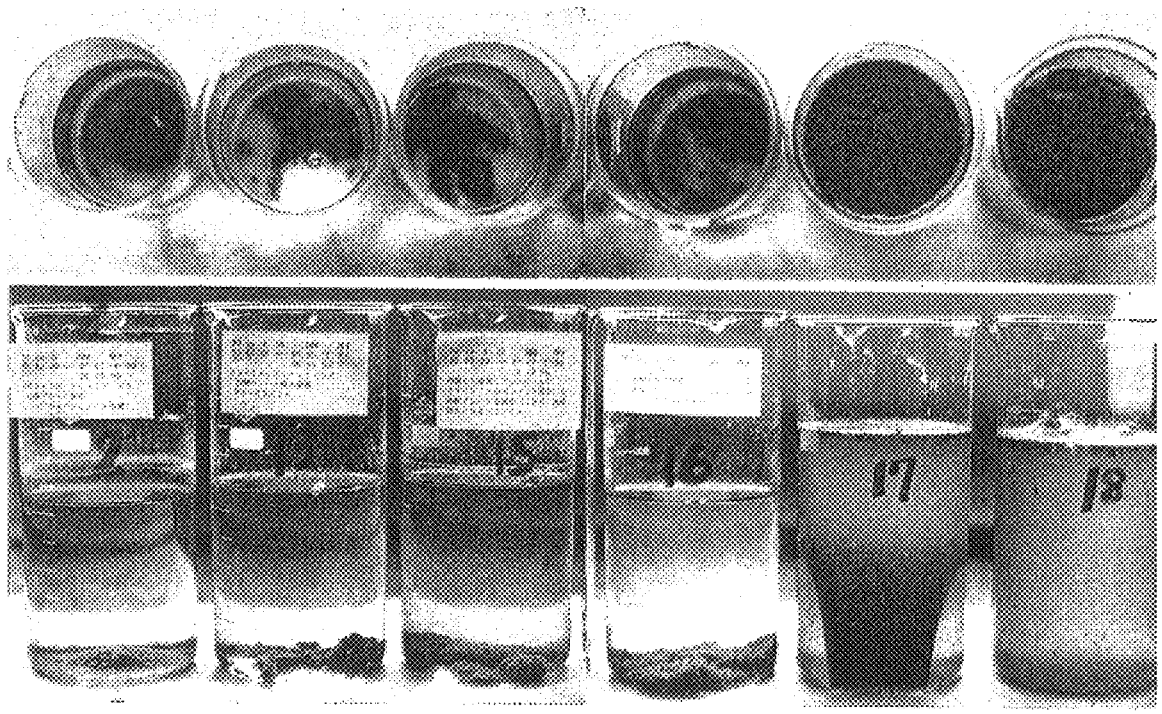
FIG. 18 are photographs of test solutions which demonstrate the algae suppressing action of a photosemiconductor-nickel containing film applied to a nickel alloy coated stainless steel strip.

A number of beakers were filled with 800 ml water containing algae collected from a rice paddy. A piece (2"×4") of photosemiconductor-conductor coated stainless steel, in this experiment a strip of Type 304 stainless steel (Fe 72 wt %, Ni 10 wt % and Cr 18 wt %), coated with an LMI film containing a nickel aluminum alloy and then with an LMI film of $TiO_2$+Ni, was immersed into one of the beakers. After 20 days, the algae inside the beaker was completely eradicated, leaving an organic carcass at the bottom of the container. The anti-microbial strip was removed after 38 days and then placed in another algae-containing beaker. After purifying the solution, toe same algae eradicating strip was dipped into yet another beaker with algae. After 184 days, 4 beakers-full of algae had been purified. On the 184th day, beaker identified as #17 was provided with the anti-algae article. Beaker #18 had not yet been treated and represented a control at that time. The sterilized beakers #2, 13, 15 and 16 were left standing and have revealed no algae growth since removal of the anti-microbial film and may be compared with beakers 17 and 18 as shown in FIG. 18. (The brownish green clots on their bottoms are algae carcass.)

Those skilled in the art will be able to ascertain, using no more than routine experimentation, many equivalents of the specific embodiments of the invention described herein. These and all other equivalents are intended to be encompassed by the following claims.

What is claimed is:

1. An article including an anti-microbial film which contains a porous network of interconnected low temperature melt injected and resolidified photosemiconductor and conductor particles wherein said anti-microbial film further includes active unmelted adsorbent particles for trapping microorganisms, said conductor particles having a melting temperature lower than a deactivating temperature of said active adsorbent particles.

2. The article recited in claim 1 wherein said article includes a conductive metal plating which is attached to said anti-microbial film.

3. The article recited in claim 1 wherein said photosemiconductor particles are selected from the group consisting of $TiO_2$, $SrTiO_3$, $KNbO_3$, CdSe, CdS, $WO_3$, $Fe_2O_3$ and mixtures thereof.

4. The article recited in claim 1 wherein said conductor particles are selected from the group consisting of Ni, Ag, Ni containing metals, Ag containing metals and mixtures thereof.

5. The article recited in claim 1 wherein said conductor particles exhibit an anti-microbial effect in darkness.

6. The article recited in claim 1 further including a water retentive member fluidly communicable with said anti-microbial film.

7. The article recited in claim 1 wherein a vapor impermeable seal is provided around said anti-microbial film.

8. The article recited in claim 1 wherein said active adsorbent particles are selected from the group consisting of apatite, zeolite, activated carbon and mixtures thereof.

9. The article recited in claim 8 wherein said active apatite adsorbent particles include hydroxyapatite.

10. The article recited in claim 1 wherein said article is a heat susceptible material.

11. The article recited in claim 10 wherein said heat susceptible material includes a surface which is electroless metal plated.

12. The article recited in claim 11 wherein said heat susceptible material is flexible.

13. The article recited in claim 1 wherein said article is a filter.

14. The article recited in claim 1 wherein said article is a bandage.

15. An article having anti-microbial properties, comprising:

a substrate;

an anti-microbial film attached to said substrate, said film including a first layer having a porous network of active unmelted adsorbent particles joined with conductive particles and a second layer having a porous network of interconnected low temperature melt injected and resolidified photosemiconductor and conductor particles, wherein said conductor particles in said first layer have a melting temperature lower than a deactivating temperature of said active adsorbent particles in said first layer.

16. The article recited in claim 15 wherein said first layer is positioned between said second layer and said substrate.

17. The article recited in claim 15 wherein said second layer is positioned between said first layer and said substrate.

18. The article recited in claim 15 wherein said first layer further includes resolidified and non-active adsorbent particles.

19. The article recited in claim 15 wherein said first layer conductive particles have a melting point which is lower than a decomposition temperature of an OH group in said active adsorbent particles.

20. The article recited in claim 15 wherein said adsorbent particles includes unmelted large active adsorption fragments and small melted and resolidified non-active adsorption fragments.

21. The article recited in claim 20 wherein said small resolidified non-adsorption active fragments secure said large active adsorption fragments to said anti-microbial film.

22. The article recited in claim 15 wherein said resolidified conductive particles in said second layer secure said adsorbent particles to said anti-microbial film.

23. The article recited in claim 15 wherein said substrate is heat susceptible.

24. The article recited in claim 23 wherein said heat susceptible substrate is flexible.

25. An article having anti-microbial properties, comprising:

a substrate;

a melt injected film attached to said substrate containing a porous network of active unmelted adsorbent particles for trapping microorganisms and melted and resolidified conductor particles which support said active unmelted adsorbent particles, wherein said conductor particles have a melting temperature lower than a deactivating temperature of said active adsorbent particles.

26. The article recited in claim 25 wherein said melted and resolidified conductor particles include non-active adsorbent particles.

27. The article recited in claim 25 wherein said conductive particles include particles having anti-microbial affect.

28. The article recited in claim 25 wherein said anti-microbial conductive particles are selected from the group consisting of silver, silver containing metals, nickel, nickel containing metals and mixtures thereof.

29. The article recited in claim 25 wherein said substrate includes a conductive coating.

30. An article having anti-microbial properties, comprising:

a substrate;

an anti-microbial film attached to said substrate, said film including a porous network of active adsorbent particles and melted and resolidified photosemiconductor and conductor particles, all of which are intimately mixed so that adsorption and sterilization functions occur.

31. The article recited in claim 30 wherein said active adsorbent particles are supported by said melted and resolidified particles.

32. The article recited in claim 31 wherein said melted and resolidified particles include non-active adsorbent particles.

33. The article recited in claim 31 wherein said melted and resolidified particles include conductive metal particles.

34. The article recited in claim 30 wherein said film includes a first layer containing active adsorbent and conductor particles and a second layer containing photosemiconductor and conductor particles.

* * * * *